(12) United States Patent
Hahn et al.

(10) Patent No.: US 8,147,855 B2
(45) Date of Patent: *Apr. 3, 2012

(54) METHODS FOR INHIBITING SENSORY RESPONSES IN THE SKIN SUCH AS PAIN AND ITCH USING TOPICAL PRODUCT FORMULATIONS CONTAINING STRONTIUM

(75) Inventors: Gary S. Hahn, Cardiff by the Sea, CA (US); David O. Thueson, Poway, CA (US)

(73) Assignee: Cosmederm Bioscience, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/654,563

(22) Filed: Dec. 23, 2009

(65) Prior Publication Data

US 2010/0173021 A1    Jul. 8, 2010

Related U.S. Application Data

(63) Continuation of application No. 11/979,154, filed on Oct. 31, 2007, now abandoned, which is a continuation of application No. 09/992,491, filed on Nov. 21, 2001, now Pat. No. 7,404,967, which is a continuation of application No. 09/871,576, filed on May 31, 2001, now abandoned, which is a continuation of application No. 09/149,886, filed on Sep. 8, 1998, now abandoned, which is a continuation of application No. 08/666,978, filed on Jun. 20, 1996, now Pat. No. 5,804,203, which is a continuation-in-part of application No. 08/362,100, filed on Dec. 21, 1994, now Pat. No. 5,716,625.

(51) Int. Cl.
  *A61K 8/02*   (2006.01)
  *A61K 8/19*   (2006.01)
(52) U.S. Cl. .......... 424/401; 424/59; 424/663; 424/673; 424/718; 424/722
(58) Field of Classification Search ................. 424/401, 424/600, 59, 663, 673, 718, 722
See application file for complete search history.

(56) References Cited

U.S. PATENT DOCUMENTS

| | | | |
|---|---|---|---|
| 1,619,076 A | 3/1927 | Kuever | |
| 2,216,816 A | 10/1940 | Kuever | |
| 2,236,387 A | 3/1941 | Wallace et al. | |
| 2,719,811 A | 10/1955 | Cook et al. | |
| 2,885,323 A | 5/1959 | Braun | |
| 3,075,880 A | 1/1963 | Roth | |
| 3,343,540 A | 9/1967 | Siegel | |
| 3,519,711 A | 7/1970 | Svigals | |
| 3,558,771 A | 1/1971 | Balassa | |
| 3,624,201 A | 11/1971 | Balassa | |
| 3,689,636 A | 9/1972 | Svajda | |
| 3,699,221 A * | 10/1972 | Schole et al. | .............. 424/54 |
| 3,716,054 A | 2/1973 | Porter et al. | |
| 3,861,868 A | 1/1975 | Milbrada | |
| 3,865,546 A | 2/1975 | Zemlin et al. | |
| 3,984,540 A | 10/1976 | Willard, Sr. | |
| 3,996,346 A | 12/1976 | Staffier et al. | |
| 4,053,630 A | 10/1977 | Yu et al. | |
| 4,062,937 A | 12/1977 | Rea | |
| 4,083,965 A | 4/1978 | Bluhm | |
| 4,105,782 A | 8/1978 | Yu et al. | |
| 4,105,783 A | 8/1978 | Yu et al. | |
| 4,160,819 A | 7/1979 | Willer et al. | |
| 4,161,522 A | 7/1979 | Hamburger | |
| 4,171,299 A | 10/1979 | Hamburger | |
| 4,185,093 A | 1/1980 | Carnes et al. | |
| 4,191,750 A | 3/1980 | Hodosh | |
| 4,235,873 A | 11/1980 | Packman | |
| 4,248,861 A | 2/1981 | Schutt | |
| 4,283,386 A | 8/1981 | Van Scott et al. | |
| 4,285,973 A | 8/1981 | Edwards | |
| 4,302,443 A | 11/1981 | deNavarre et al. | |
| 4,320,114 A | 3/1982 | Denzinger et al. | |
| 4,323,558 A | 4/1982 | Nelson | |
| 4,331,653 A | 5/1982 | Brown et al. | |
| 4,363,794 A | 12/1982 | Ochiai et al. | |
| 4,367,224 A | 1/1983 | Van Scott et al. | |
| 4,370,325 A | 1/1983 | Packman | |
| 4,388,301 A | 6/1983 | Klein | |
| 4,477,439 A | 10/1984 | D'Alelio | |
| 4,507,321 A | 3/1985 | Raisfield | |
| 4,529,593 A | 7/1985 | Warrell, Jr. et al. | |
| 4,551,330 A | 11/1985 | Wagman et al. | |

(Continued)

FOREIGN PATENT DOCUMENTS

| | | | |
|---|---|---|---|
| AU | 1785492 A | | 12/1992 |
| CA | 1 192 493 A1 | | 8/1985 |
| CA | 1 331 009 C | | 7/1994 |
| DE | 2 362 268 | | 7/1974 |
| DE | 26 57 896 A1 | | 7/1978 |
| DE | 42 26 736 A1 | | 2/1994 |
| EP | 0 85 579 A2 | | 8/1983 |
| EP | 0 100 827 A2 | | 2/1984 |
| EP | 0 132 126 A1 | | 1/1985 |
| EP | 0 137 743 A2 | | 4/1985 |

(Continued)

OTHER PUBLICATIONS

Zyuzyukin, Y., et al., "Local Action of Strontium Compounds," Chemical Abstracts, (1973), pp. 100-101, vol. No. 12, Abstract No. 80:78918.

(Continued)

*Primary Examiner* — Gina C Yu
(74) *Attorney, Agent, or Firm* — Gordon & Rees LLP; Laurie A. Axford

(57) ABSTRACT

Methods for inhibiting sensory responses in the skin such as pain and itch using topical formulations containing aqueous-soluble divalent strontium cation in a suitable topical keratinized skin formulation vehicle are disclosed.

11 Claims, 13 Drawing Sheets

U.S. PATENT DOCUMENTS

| | | | |
|---|---|---|---|
| 4,579,840 A | 4/1986 | Hahn | |
| 4,626,433 A | 12/1986 | Gros | |
| 4,628,045 A | 12/1986 | Hahn | |
| 4,663,165 A | 5/1987 | Revici | |
| 4,683,292 A | 7/1987 | Hahn | |
| 4,686,104 A | 8/1987 | Bockman et al. | |
| 4,686,282 A | 8/1987 | Hahn | |
| 4,692,511 A | 9/1987 | Hahn | |
| 4,704,234 A | 11/1987 | Petersen et al. | |
| 4,704,277 A | 11/1987 | Bockman et al. | |
| 4,732,892 A | 3/1988 | Sarpotdar et al. | |
| 4,735,802 A | 4/1988 | Le | |
| 4,743,442 A | 5/1988 | Raaf et al. | |
| 4,772,591 A | 9/1988 | Meisner | |
| 4,816,449 A | 3/1989 | Hahn | |
| 4,840,798 A | 6/1989 | Skaliotis | |
| 4,859,653 A | 8/1989 | Morelle et al. | |
| 4,868,213 A | 9/1989 | Farrish | |
| 4,879,116 A | 11/1989 | Fox et al. | |
| 4,917,889 A | 4/1990 | Carty et al. | |
| 4,939,164 A | 7/1990 | Wierzbicki et al. | |
| 4,943,432 A | 7/1990 | Biener | |
| 4,971,800 A | 11/1990 | Chess et al. | |
| 5,039,529 A | 8/1991 | Bergendal et al. | |
| 5,053,219 A | 10/1991 | Giddey et al. | |
| 5,061,692 A | 10/1991 | Hahn | |
| 5,075,336 A | 12/1991 | Czernecki et al. | |
| 5,079,010 A | 1/1992 | Natterer | |
| 5,087,444 A * | 2/1992 | Jackson et al. | 424/49 |
| 5,091,171 A | 2/1992 | Yu et al. | |
| 5,098,716 A | 3/1992 | Embro | |
| 5,102,670 A | 4/1992 | Abraham et al. | |
| 5,110,795 A | 5/1992 | Hahn | |
| 5,118,665 A | 6/1992 | Pickart | |
| 5,126,135 A | 6/1992 | Yamada et al. | |
| 5,128,367 A | 7/1992 | Wierzbicki et al. | |
| 5,153,230 A | 10/1992 | Jaffery | |
| 5,252,322 A | 10/1993 | Stoner et al. | |
| 5,262,153 A | 11/1993 | Mishima et al. | |
| 5,279,837 A | 1/1994 | Hill | |
| 5,286,490 A | 2/1994 | Grodberg | |
| 5,296,476 A | 3/1994 | Henderson | |
| 5,348,733 A | 9/1994 | Morishima et al. | |
| 5,360,824 A | 11/1994 | Barker | |
| 5,407,958 A | 4/1995 | Heath et al. | |
| 5,411,731 A | 5/1995 | Tanaka et al. | |
| 5,411,734 A | 5/1995 | Vargas et al. | |
| 5,422,101 A | 6/1995 | Daggy et al. | |
| 5,433,942 A | 7/1995 | Wood et al. | |
| 5,439,682 A | 8/1995 | Wivell et al. | |
| 5,443,847 A | 8/1995 | West | |
| 5,468,730 A | 11/1995 | Hahn | |
| 5,470,563 A | 11/1995 | Tanaka et al. | |
| 5,476,647 A | 12/1995 | Chow et al. | |
| 5,480,975 A | 1/1996 | Goldberg et al. | |
| 5,482,710 A | 1/1996 | Slavtcheff et al. | |
| 5,520,918 A * | 5/1996 | Smith | 424/401 |
| 5,624,415 A | 4/1997 | Cormier et al. | |
| 5,656,280 A | 8/1997 | Herb et al. | |
| 5,658,586 A | 8/1997 | Rajaiah et al. | |
| 5,662,941 A | 9/1997 | Bourbon et al. | |
| 5,674,505 A | 10/1997 | Levere et al. | |
| 5,686,116 A | 11/1997 | Bockman et al. | |
| 5,709,849 A | 1/1998 | Ito et al. | |
| 5,716,625 A | 2/1998 | Hahn et al. | |
| 5,804,203 A | 9/1998 | Hahn et al. | |
| 5,824,650 A | 10/1998 | De Lacharriere et al. | |
| 5,851,556 A | 12/1998 | Breton et al. | |
| 5,866,168 A | 2/1999 | De Lacharriere et al. | |
| 5,912,233 A | 6/1999 | Hahn | |
| 5,958,436 A | 9/1999 | Hahn et al. | |
| 5,972,892 A | 10/1999 | De Lacharriere et al. | |
| 6,165,514 A | 12/2000 | Bockman et al. | |
| 6,267,962 B1 | 7/2001 | Hart et al. | |
| 6,287,606 B1 | 9/2001 | Bockman et al. | |
| 6,319,850 B1 | 11/2001 | Chang et al. | |
| 6,455,076 B1 | 9/2002 | Hahn et al. | |
| 2003/0031727 A1 | 2/2003 | Hahn et al. | |

FOREIGN PATENT DOCUMENTS

| | | |
|---|---|---|
| EP | 0 165 430 A1 | 12/1985 |
| EP | 0 217 975 A1 | 4/1987 |
| EP | 0 253 083 A2 | 1/1988 |
| EP | 0 311 260 A2 | 4/1989 |
| EP | 0 346 957 A1 | 12/1989 |
| EP | 0 354 447 A2 | 2/1990 |
| EP | 0 393 456 A2 | 10/1990 |
| EP | 0 423 929 A1 | 4/1991 |
| EP | 0 424 033 A2 | 4/1991 |
| EP | 0 432 700 A2 | 6/1991 |
| EP | 439 640 A1 | 8/1991 |
| EP | 0 469 813 A2 | 2/1992 |
| EP | 0 471 392 A2 | 2/1992 |
| EP | 0 484 112 A2 | 5/1992 |
| EP | 0 520 112 A1 | 12/1992 |
| EP | 0 559 262 A1 | 9/1993 |
| EP | 0 654 270 A1 | 5/1995 |
| EP | 0 671 162 A2 | 9/1995 |
| EP | 0 801 554 A1 | 10/1997 |
| EP | 1 136 065 A1 | 9/2001 |
| FR | 5.394 M | 9/1967 |
| FR | 6548 M | 1/1969 |
| FR | 2 047 885 A1 | 3/1971 |
| FR | 2 122 613 A | 9/1972 |
| FR | 2 291 740 A1 | 6/1976 |
| FR | 2 361 904 A1 | 3/1978 |
| FR | 2 482 680 A1 | 11/1981 |
| FR | 2 590 273 A1 | 5/1987 |
| FR | 2 725 901 A1 | 4/1996 |
| GB | 1 072 355 | 6/1967 |
| GB | 1 122 796 A | 8/1968 |
| GB | 1 160 640 A | 8/1969 |
| GB | 1 334 933 | 10/1973 |
| JP | 46-035760 | 10/1971 |
| JP | 53-121007 A | 10/1978 |
| JP | 54-163819 A | 12/1979 |
| JP | 61-109725 A | 5/1986 |
| JP | 62-255406 A | 11/1987 |
| JP | 63-215635 A | 9/1988 |
| JP | 2-157210 A | 6/1990 |
| JP | 4-005224 A | 1/1992 |
| JP | 5-123398 A | 5/1993 |
| JP | 117158 A | 5/1993 |
| JP | 5-221823 A | 8/1993 |
| JP | 6-080544 A | 3/1994 |
| JP | 6-135840 A | 5/1994 |
| JP | 7-267869 A | 10/1995 |
| JP | 7-267870 A | 10/1995 |
| JP | 11-502504 | 3/1999 |
| WO | WO 89/06133 A1 | 7/1989 |
| WO | WO 91/19491 A1 | 12/1991 |
| WO | WO 92/08777 A1 | 5/1992 |
| WO | WO 92/09291 A1 | 6/1992 |
| WO | WO 93/10776 | 6/1993 |
| WO | WO 93/25211 A1 | 12/1993 |
| WO | WO 94/03147 | 2/1994 |
| WO | WO 94/06440 | 3/1994 |
| WO | WO 94/09798 A1 | 5/1994 |
| WO | WO 94/13305 A1 | 6/1994 |
| WO | WO 95/26198 A1 | 10/1995 |
| WO | WO 96/19184 | 6/1996 |

OTHER PUBLICATIONS

The Merck Index, 11$^{th}$ Ed., (1989), pp. 1394-1395.

Bilotto, Gerardo, et al., "Effects of Ionic and Non-Ionic Solutions on Intradental Nerve Activity in the Cat," Pain, (1988) pp. 231-238, vol. No. 32.

Celerier, et al., "Modulatory Effects of Selenium and Strontium Salts on Keratinocyte-Derived Inflammatory Cytokines," Arch. Dermatol. Res., (1985), pp. 680-682, vol. No. 287.

Foreman, J.C., et al., "Movement of Strontium Ions into Mast Cells and its Relationship to the Secretory Response," J. Physiol., (1977), pp. 233-251, vol. No. 271.

Frankenhaeuser, Bernard, et al., "The Effect of Magnesium and Calcium on the Frog Myelinated Nerve Fiber," J. Physiol., (1958), pp. 360-365, vol. No. 142.

Gutentag, Herb, "The Effect of Strontium Chloride on Peripheral Nerve in Comparison to the Action of 'Stabilizer' and 'Labilizer' Compounds," Penn. Dental Journal, (Feb. 1995), pp. 37-43, vol. No. 68.

Kato, G., et al., "Anesthetic Action of Magnesium Ions," Can. Anaes. Soc. J., (Nov. 1968), pp. 539-544, vol. No. 15.

Katz, Irving H., "Tropical Corticosteroids," Dermatologic Clinics, (Oct. 1995), pp. 897-907, vol. No. 13.

Kim, Syngcuk, "Hypersensitive Teeth" Desensitization of Pulpal Sensory Nerves, J. Endodontics, (Oct. 1986), pp. 482-485, vol. No. 12.

Markowitz, K., et al., "Decreasing Intradental Nerve Activity in the Cat with Potassium and Divalent Cations," Archs. Oral Biol., (1991), pp. 1-7, vol. No. 36.

Markotwitz, K., et al., "The Role of Selected Cations in the Desensitization of Intradental Nerves," Proc. Finn. Dent. Soc., (1992), pp. 39-54, vol. No. 88.

Orchardson, R., "Is Calcium More Effective than Strontium as a Desensitizing Agent for Dentine?" Lesney & Matthew eds., Current Topics in Oral Biology, (1985), pp. 205-215, University of Bristol Press.

Penny, Deborah, et al., "Fast Desensitization of Tooth Roots by Topically Applied $SnF_2$ and $SrCl_2$ in Dogs," Archs. Oral Biol., (1976), pp. 339-347, vol. No. 21.

Shioya, Takao, et al., "Fast and Slow Blockades of the Inward-Rectifier $K^+$ Channel by External Divalent Cations in Guinea-Pig Cardiac Myocytes," Pflugers Arch., (1993), pp. 427-435, vol. No. 422.

Sohn, et al., "Agonist-Independent, Muscle-Type-Specific Signal Transduction Pathways in Cat Esophageal and Lower Esophageal Sphincter Circular Smooth Muscle," J. Pharmacol. & Exp. Therap., (1995), pp. 482-491, vol. No. 273.

Sohn, et al., Different Receptors Activate a Different Single G-Protein in Esophageal ($G_{i3}$) and LES ($G_q$) Circular Smooth Muscle, Gastroenterology, (Apr. 1993), Abstract pp. A585, vol. No. 104.

Abel, Elizabeth A., "Phototherapy," Dermatologic Clinics, (Oct. 1995), pp. 841-849, vol. No. 13.

Arky, Ronald, et al., (Eds.) Physicians Desk Reference, $49^{th}$ Edition, (1995), pp. 929.

Fitzpatrick, Thomas B., et al., (Eds.), Dermatology in General Medicine, (1993), pp. 501, 508-510, 1393-1396, vol. No. 1, McGraw-Hill, Inc.

Gilman, Alfred G., et al., "The Pharmacological Basis of Therapeutics," (1993), pp. 769-771, 1291, 1518-1519, 1581-1586, McGraw-Hill, Inc.

Gonzalez, Ernesto, "PUVA for Psoriasis," Dermatological Clinics, (Oct. 1995), pp. 851-866, vol. No. 13.

Greaves, Malcolm E., et al., "Treatment for Psoriasis," New England J. Med., (Mar. 1995), pp. 581-588, vol. No. 332.

Griffiths, Tamara W., et al., "Immunopathogenesis and Immunotherapy of Psoriasis," Dermatological Clinics, (Oct. 1995), pp. 739-749, vol. No. 13.

Hahn, et al., J. Allerg. Clin. Immunol., (1990), pp. 85 (1 part 2) vol. No. 298.

Jeffes III, Edward W.B., et al., "Methotrexate and Other Chemotherapeutic Agents Used to Treat Psoriasis," Dermatologic Clinics, (Oct. 1995), pp. 875-890, vol. No. 13.

Katz, Irving H., "Topical Corticosteroids," Dermatologic Clinics, (Oct. 1995) pp. 805-815, vol. No. 13.

Kelly, J.S., et al., "Divalent Cations and Electrical Properties of Cortical Cells," J. Neurobiol., (1969), pp. 197-208, vol. No. 2.

Koo, John, et al., "Cyclosporine: What Clinicians Need to Know," Dermatologic Clinics, (Oct. 1995), pp. 897-907, vol. No. 13.

Kragballe, Knud, "Vitamin D3 Analogues," Dermatologic Clinics, (Oct. 1995), pp. 835-839, vol. No. 13.

Krnjevic, K., "Actions of Drugs on Single Neurones in the Cerebral Cortex," Brit. Med. Bull., (1965), pp. 10-14, vol. No. 21.

Lebwohl, Mark, "Future Psoriasis Therapy," Dermatologic Clinics, (Oct. 1995), pp. 915-923, vol. No. 13.

Lovaas, "Hypothesis: Spermine May be an Important Epidermal Antioxidant," Medical Hypotheses, (1995), pp. 59-67, vol. No. 45.

Momtaz-T., Khosrow, "Modification of PUVA," Dermatologic Clinics, (Oct. 1995), pp. 867-873, vol. No. 13.

Silverman, A.K., et al., "Tars and Anthralins," Dermatologic Clinics, (Oct. 1995), pp. 816-834, vol. No. 13.

Wieder, Joshua M., et al., "Systemic Retinoids for Psoriasis," Dermatologic Clinics, (Oct. 1995), pp. 891-896, vol. No. 13.

Armstrong, C.M., et al., "The Role of Calcium Ions in the Closing of K Channels," J. Gen. Physiol., (May 1986), pp. 817-832, vol. No. 87.

Drodiak, W., "Keeping Svelte and Healthy With Vitamin Sea," The Washington Post, (Mar. 25, 1996), Section A, pp. 11.

Kato, G., et al., "Effects of Micro-Iontophoretic Administration of Magnesium and Calcium on Nuerones in the Central Nervous System of Cats," J. Neurobiol., (1969), pp. 181-195, vol. No. 2.

Kelly, J.S., et al., "Divalent Cations and Electrical Properties of Cortical Cells," J. Neurobiol., (1969), pp. 197-208, vol. No. 2.

Markowitx, Kenneth, et al., "Decreasing Intradental Nerve Activity in the Cat with Potassium and Divalent Cations," Archs. Oral Biol., (1992), pp. 1-7, vol. No. 36.

Marrero, H., et al., "Facilitation of Sodium Currents in Frog Neuroglia by Nerve Impulses: Dependence on External Calcium," Proc. R. Soc. Lond. B, (1993), pp. 219-224, vol. No. 253.

Narhi, M.V.O., et al., "Activation of Intradental Nerves in the Dog to Some Stimuli Applied to the Dentine," Archs. Oral Biol., (1982), pp. 1053-1058, vol. No. 27.

Bayless, Mark J., et al., "Diagnosis and Treatment of Acute Fluoride Toxicity," Am. Dental Ass'n., (Feb. 1995), pp. 209-211, vol. No. 110.

Budavari, Susan, et al., (Eds.) The Merck Index, (1989), pp. 708, 1218, Merck & Co., Inc.

Brooks, et al., "Cutaneous Allergy to Insulin Preparations," Pract. Diabetes, (1994), pp. 236-238, vol. No. 11.

Cohen, et al., "Safety and Efficacy of Human IgE Pentapeptide," Ann. Allergy, (1984), pp. 83-86, vol. No. 52.

Degroot, "Unwanted Effects of Cosmetics and Drugs Used in Dermatology," (1995), pp. 229.

Dolynchuk, et al., "Topical Purtescine (Fibrostat) in Treatment of Hypertropic Scars: Phase II Study," Plast. Reconstr. Surg., (Jan. 1996), pp. 117-123, vol. No. 97.

"Drug Facts and Comparisons", (1995), pp. 37-38, Facts and Comparisons, St. Louis MO.

Hallmans, Goran, "Local Absorption of Zinc from Wounds Treated with Different Concentrations of Zinc Sulphate," Acta Dermatovener, (1978), pp. 413-419, vol. No. 58, Stockholm.

Harris, Adron R., et al., "Antinociceptive Effects of Lanthanum and Cerium in Nontolerant and Morphine Tolerant-Dependent Animals," J. Pharmacol. Exp. Ther., (1976), pp. 288-297, vol. No. 196.

Harris, Adron R., et al., "Effects of Divalent Cations, Cation Chelators and Ionophore on Morphine Analgesia and Tolerance," J. Pharmacol. Exp. Ther., (1975), pp. 488-498, vol. No. 195.

Landsdown, A.B.G., "Interspecies Variations in Response to Topical Application of Selected Zinc Compounds," Food Chem. Toxic, (1991), pp. 57-64, vol. No. 29.

Lowe. Nicholas J., et al., "Generalized Pustular Psoriasis Precipitated by Lithium Carbonate," Arch. Dermatol., (Dec. 1978), pp. 1788-1789, vol. No. 114.

Morris, Christopher J., et al., "Reactive Oxygen Species and Iron a Dangerous Partnership in Inflammation," Int. J. Biochem. Cell Biol., (1995), pp. 109-122, vol. No. 27.

Oota, et al., Antimicrobial Composition Containing Iodine and Arginine Derivatives, Chemical Abstracts, (Aug. 1996) Abstract No. 105082 (XP002074366) vol. No. 125, Columbus, Ohio.

Piacentini, M., et al., "Free and Protein-Conjugated Polyamines in Mouse Epidermal Cells: Effect of High Calcium and Retinoic Acid," J. Biol. Chem., (Mar. 1988), Medline Abstract No. 88153675, pp. 3790-3794, vol. No. 263.

Salvato, Anthony R., et al., "Clinical Effectiveness of a Dentifrice Containing Potassium Chloride as a Desensitizing Agent," Am. J. Dent., (Dec. 1992), pp. 303-306, vol. No. 5.

Sasaki, H., et al., "Enhancing Effect of Pyrrolidone Derivatives on Transdermal Penetration of Phenolsulfonphthalein and Indomethacin from Aqueous Vehicle," Chem. Pharm. Bull., (Mar. 1990), pp. 797-799, vol. No. 38.

Serup, Jorgen, et al., "Epidermal Hydration of Psoriasis Plaques and the Relation to Scaling: Measurement of Electrical Conductance and Transepidermal Water Loss," Acta Derm Venereol, (1987), pp. 357-359, vol. No. 67, Stockholm.

Tagmi, Hachiro, et al., "Interrelationship Between Water-Barrier and Reservoir Functions of Pathologic Stratum Corneum," Arch. Dermatol., (May 1985), pp. 642-645, vol. No. 121.

Takata, M., et al., "Ionic Conductance Changes in Lobster Axon Membrane When Lanthanum is Substituted for Calcium," J. Gen. Physiol., (1966), pp. 461-471, vol. No. 50.

Tzehoval, et al., "Immunopathol," Springer Sermin., (1979), pp. 205-214, vol. No. 2.

Viluksela, M., "Characteristics and Modulation of Dithranol (Anthralin)—Induced Skin Irritation in the Mouse Ear Model," Archives of Dermatological Research, (1991), Abstract No. 9202794, pp. 262-268, vol. No. 283.

Von Den Driesch, P., et al., "Fulminant Acne: Therapy with 13-cis-Retinoic Acid and Indomethacin," Zeitschrift fur Hautkrankheiten, (Aug. 1986,) pp. 1145-1151, vol. No. 61.

Wilkinson, J.B., et al., (Eds.) Harry's Cosmeticology, (1982), pp. 74, Chemical Publishing Company, New York, New York.

Wilhelm, K.P., et al., "Effect of Sodium Lauryl Sulfate-Induced Skin Irritation on In Vivo Precutaneous Penetration of Four Drugs," Journal of Investigative Dermatology, (Nov. 1991) Abstract No. 92013249, pp. 927-932, vol. No. 97.

Spets-Happonen, et al., "The Effect of Different Strontium Concentrations on the Efficacy of Chlorhexidine-Fluoride-Strontium Gel in Preventing Enamel Softening in Vitro," Arch. Oral Biol., (1993), pp. 107-112, vol. No. 38, PMID 8476339.

Kun, L., "Biophysical Study of Dental Tissues Under the Effect of a Local Strontium Application," SSO Schweiz Monatsschr Zahnheilkd, (1976), pp. 661-676, vol. No. 86, PMID 1066811.

Grynpas, et al., "Effects of Low Doses of Strontium on Bone Quality and Quantity in Rats," Bone, (1990) pp. 313-319, vol. No. 11, PMID 2252809.

Grynpas, et al., "Strontium Increases Vertebral Bone Volume in Rats at a Low Dose That Does Not Induce Detectable Mineralization Defect," Bone, (1996) pp. 253-259, vol. No. 18, PMID 8703581.

Marie, et al., "Effects of Low Doses of Stable Strontium on Bone Metabolism in Rats," Miner Electrolyte Metab., (1985) pp. 5-13, vol. No. 11, PMID 3974537.

Marie, et al., "Short Term Effects of Fluoride and Strontium on Bone Formation and Resporption in the Mouse," Metabolism, (1986) pp. 547-551, vol. No. 35.

"Strontium Sulfide," Cameo Chemical Data Sheet.

Winter, Ruth A., (Ed.), "A Consumer's Dictionary of Cosmetic Ingredients," (1989) pp. 32-33, $3^{rd}$ edition, Crown Publishers, New York.

Olson, K., et al., "Poising & Drug Overdose," (2004) pp. 575, $4^{th}$ Ed., McGraw-Hill Companies, Inc.

Blacow, et al., "Martindale: The Extra Pharmacopoeia," The Pharmaceutical Press, (1972) pp. 241 and 1699, $26^{th}$ Ed., London.

Shafer, et al., "Tin-A Toxic Heavy Metal?" Regulatory Toxicology and Pharmacology, (1984) pp. 57-69, vol. No. 4, Academic Press, Inc., USA.

Skoven, et al., "Lithium Compound Treatment and Psoriasis," Archives of Dermatology, (1979) pp. 1185-1187, vol. No. 115, No. 10, American Medical Association, USA.

* cited by examiner

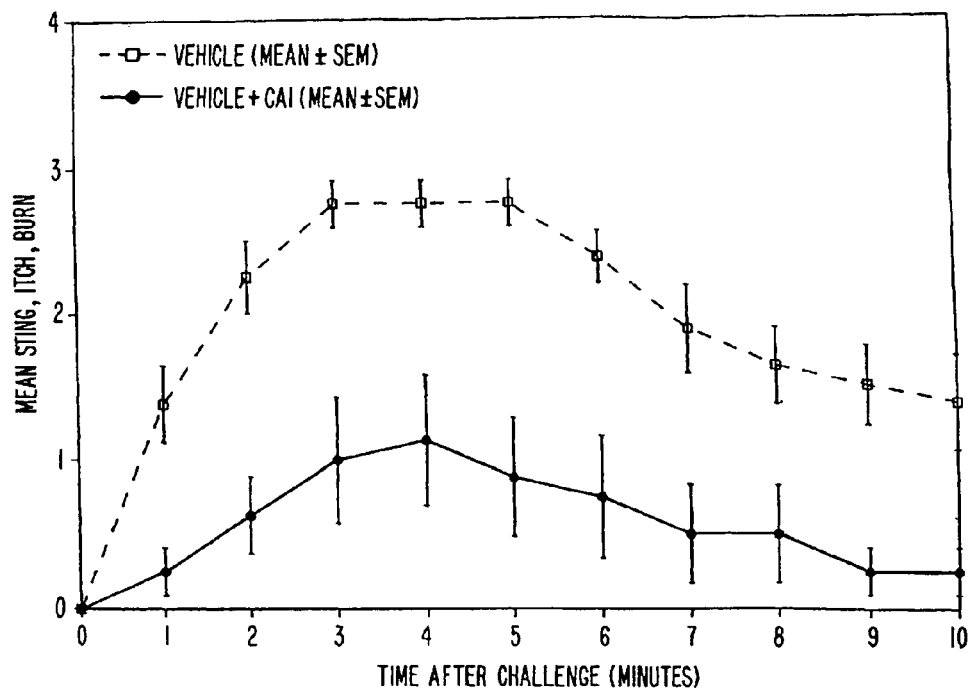
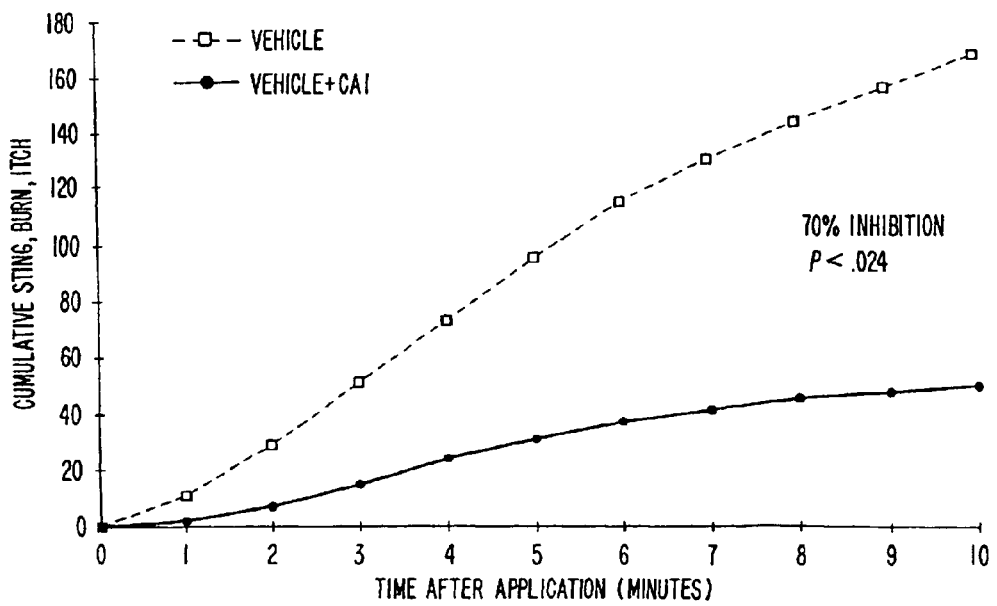

METHODS FOR INHIBITING SENSORY RESPONSES IN THE SKIN SUCH AS PAIN AND ITCH USING TOPICAL PRODUCT FORMULATIONS CONTAINING STRONTIUM

This application is a continuation of Ser. No. 11/979,154, filed Oct. 31, 2007, Ser. No. 09/992,491, filed Nov. 21, 2001, Ser. No. 09/871,576, filed May 31, 2001, Ser. No. 09/149,886, filed Sep. 8, 1998, which is a continuation of Ser. No. 08/666,978, filed Jun. 20, 1996, and issued as U.S. Pat. No. 5,804,203, which is a continuation-in-part of Ser. No. 08/362,100, filed Dec. 21, 1994, and issued as U.S. Pat. No. 5,716,625. The present application claims the benefit of the filing date of Ser. No. 08/362,100 (Dec. 21, 1994), as well as the benefit of all intervening applications, pursuant to 35 U.S.C. §120 and other applicable law, and the entire disclosures of all of these applications are incorporated herein by reference in their entirety.

BACKGROUND

Many substances are applied topically to the skin or mucous membranes of humans or animals (hereinafter "skin") in order to alter the subject's appearance, to protect the subject from the environment, or to produce a biological change in the skin or other tissue for therapeutic, preventive or cosmetic purposes. These substances may generically be termed "topical products" and include such topically applied substances as cosmetics, over-the-counter and prescription topical drugs, and a variety of other products such as soaps and detergents.

Topical products occur in a variety of forms, including solids, liquids, suspensions, semisolids (such as creams, gels, lotions, pastes or "sticks"), powders or finely dispersed liquids such as sprays or mists. Examples of topical products commonly classified as "cosmetics" include skin care products such as moisturizing creams and lotions, and "treatment cosmetics" such as exfoliants and/or skin cell renewal agents; fragrances such as perfumes and colognes, and deodorants; shaving-related products such as creams, "bracers" and aftershaves; depilatories and other hair removal products; skin cleansers, toners and astringents; pre-moistened wipes and washcloths; tanning lotions and sunscreens; bath products such as oils; eye care products such as eye lotions and makeup removers; foot care products such as powders and sprays; skin colorant and make-up products such as foundations, blushes, rouges, eye shadows and liners, lip colors and mascaras; lip balms and sticks; hair care and treatment products such as shampoos, conditioners, colorants, dyes, bleaches, straighteners, and permanent wave products; baby products such as baby lotions, oils, shampoos, powders and wet wipes; feminine hygiene products such as deodorants and douches; skin or facial peels applied by dermatologists or cosmeticians; and others. Examples of topical products commonly classified as "topical drugs" are many and varied, and include over-the-counter and/or prescription products such as antiperspirants, insect repellents, sunscreens and sunburn treatments, anti-acne agents, antibiotics, therapeutic retinoids, anti-dandruff agents, external analgesics such as capsaicin products, topical contraceptives, topical drug delivery systems, suppositories and enemas, hemorrhoid treatments, vaginal treatments, lozenges, and many other products with therapeutic or other effects. Other topical products include hand, facial and body soaps and detergents and other forms of skin cleansers, as well as household detergents and many other household products such as solvents, propellants, polishes, lubricants, adhesives, waxes and others which are either applied topically or are topically exposed to the body during normal use.

In a large number of cases, topical products contain chemicals which may produce irritation or inflammation when applied to the skin or mucosa. The present invention is directed in part to compositions for inhibiting the irritation associated with such topical products.

The occurrence, frequency and nature of topical-product-induced irritation often varies from user to user. The severity of irritation to the susceptible user may range from subclinical to mild to severe. Typical symptoms of irritation include itching (pruritus), stinging, burning, tingling, "tightness," erythema (redness) or edema (swelling). The irritation response may be due to the direct effect on the skin of certain topical product chemicals or to a response by the immune system directed toward the chemicals alone or in combination with skin components (e.g. allergic dermatitis).

The sensation of itch is one of the most common skin problems experienced by humans and animals. Itch can be defined as a sensation which provokes the desire to scratch the site from which the sensation originates. All skin contains sensory nerves which transmit itch in response to chemical irritation, environmental exposure or disease processes. Although the precise population of itch producing nerves have not been identified, the thinnest, unmyelinated nerve population, termed type C nociceptive neurons are thought to be the most important in producing the sensation. *Itch: Mechanisms and Management of Pruritus*, Jeffrey D. Bernhard, McGraw-Hill, Inc. (San Francisco, 1994), pp. 1-22. The itch-producing nerves of the skin can be considered to be a "final common pathway" for the many irritating conditions which are ultimately sensed as itch including chemical exposure, environmental exposure (such as that which produces dry, itchy skin) and disease processes such as atopic dermatitis. Many chemical substances are able to produce itch when topically applied to the skin. No matter what the ultimate cause of itch, the sensation experienced is the same and provokes the desire to scratch.

Many ingredients used in topical products are known irritants or are potentially irritating, especially to people with "sensitive skin". These irritating ingredients include fragrances, preservatives, solvents, propellants and many other ingredients that might otherwise be considered inertcomponents of the products. Additionally, many topical product active ingredients, including chemicals that may also be classified as drugs, produce irritation when applied to the skin. These include, but are not limited to, such ingredients as exfoliants and skin cell renewal agents, anti-acne drugs, antiperspirant compounds, antihistamines, anti-inflammatory agents, skin protective agents, insect repellent chemicals, sunscreens and many others. Where more than one chemical irritant is present, their irritating effects may be additive. Furthermore, chemical ingredients may react with one another, or in the environment of the skin, to form new chemicals which are irritating. The vehicles in which the active drug ingredients are formulated may also produce irritation in sensitive people, especially in drugs such as topical corticosteroids.

In addition to chemicals which directly trigger skin irritation, some chemicals indirectly cause the skin to become more sensitive to other chemicals or environmental conditions which would not normally cause irritation. Many chemicals which act as skin "exfoliants" such as retinoids (e.g. tretinoin, retinol and retinal), carboxylic acids including α-hydroxy acids (e.g. lactic acid, glycolic acid), β-hydroxy acids (e.g. salicylic acid), α-keto acids, acetic acid and trichloroacetic acid, 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, benzoyl peroxide and phenol, among others, may cause the skin to become more sensitive to irritation triggered by other topically-applied chemicals such as moisturizers, sunscreens, fragrances, preservatives, surfactants (e.g. soaps, shaving cream) and other topical products. Exfoliants and other ingredients may also increase the skin's sensitivity to environmental conditions such as sunlight, wind, cold temperature and dry air, or may exacerbate the irritation attributable to a pre-existing skin disease.

Conversely, environmental influences may themselves increase the skin's sensitivity to chemicals in topical products by reducing the skin's "barrier function." The barrier function acts to minimize absorption or passage of potentially irritating chemicals through the outer "dead" cell layer into the living skin tissue. Extremes of humidity, for example, can greatly increase irritation from topically-applied products. A very common condition due to low humidity is termed "winter itch" in which the very low humidity characteristics of many cold Climates (particularly when accompanied by indoor heating) or long exposure to refrigerated air from air conditioners in the summer produces itchy skin—especially in older people—which can exacerbate the irritating effects of topical products. Additionally, soaps, detergents, cleansing products, shaving creams, alcohol and other products which remove some of the skin's protective lipids and/or secretions may increase the skin's permeability and sensitivity to topically-applied chemicals which would otherwise not produce irritation. Normal processes such as sweating may also increase the ability of irritant materials, such as antiperspirants, deodorants or sunscreens, to penetrate the skin through pores or glands, thus exacerbating the potential for irritation. Exposure of the skin to high humidity environments or liquids may also increase the ability of potential irritants to penetrate the skin. Similarly, the skin may become sensitized or inflamed due to infection, shaving abrasion, repeated or excessive washing or bathing, sun exposure, or other mechanical abrasion or injury, resulting in sensory irritation responses upon subsequent application of underarm deodorants, after-shaves or other topical products.

In addition to chemical and environmental causes of skin irritation, many people have an inherent sensitivity or genetic predisposition to skin irritants. People with respiratory allergies, for example, tend to have excessively dry skin which facilitates increased absorption of potentially irritating chemicals. The excessively dry skin which accompanies atopic dermatitis, for example, predisposes patients with this condition to irritation from many topically-applied products. Other skin diseases and conditions such as allergic or non-allergic contact dermatitis, psoriasis, eczema, *candida albicans*, post-herpetic neuralgia, infectious diseases manifested by, for example, sore throat or skin lesions, insect bites and the like produce intrinsic irritation which may be exacerbated by application of topical products. Many other individuals exhibit sensitive skin as a condition that is not related to an identifiable skin disease.

Whatever the exact cause of irritation, many attempts have been made to reduce the irritation potential of topical products by identifying chemicals which tend to cause irritation and reducing their concentration or eliminating them from the products. Many of these products are advertised to consumers as "hypoallergenic" or the like to designate a product's reduced tendency to cause irritation in consumers with sensitive skin. Most skin or mucosal irritation responses, however, are not allergic in origin. In any event, it is often not feasible or practical to identify or eliminate all of the irritating chemical(s), particularly when the irritating chemicals) are the active ingredient of the product or are required for formulation, preservative or other functional reasons.

As one example, there is a substantial practical and commercial need in the field of exfoliants and related skin care products for a composition or method that will reduce or prevent the irritation caused by such products. Common exfoliants include α- and β-hydroxy carboxylic acids such as lactic acid, glycolic acid, salicylic acid and the like, α-keto acids such as pyruvic acid, as well as assorted compounds such as acetic acid and trichloroacetic acid, 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, peroxides, phenols, and skin cell renewal agents such as retinoids. Such products are used as exfoliants and/or cell renewal agents to reduce the occurrence or severity of skin wrinkles, particularly facial wrinkles, or as anti-acne; anti-"dry skin" or skin whitening agents. See U.S. Pat. Nos. 4,105,782, 4,105,783, 4,246,261, and 5,091,171 (Yu et al.) and 5,262,153 (Mishima et al.); W. P. Smith, "Hydroxy Acids and Skin Aging," Soap/Cosmetics/Chemical Specialties for September 1993, p. 54 (1993). Hydroxy acids, in concentrations high enough to exfoliate, are well known often to cause skin irritation and rashes. The danger of irritation is even higher for persons that have sensitive skin.

Currently available methods reported by Yu et al. to reduce the irritation caused by hydroxy- and keto-acids in topical products include adding a strong alkali metal base such as sodium hydroxide or potassium hydroxide, thereby raising the pH of the preparation and reducing the acidity of the hydroxy acid. Such methods have the reported drawback of reducing the ability of the resulting hydroxy acid salt to penetrate the skin and thus compromising the beneficial effects (particularly anti-acne or anti-"dry skin" effects) of the hydroxy acid. Alternatively, Yu et al. have proposed the approach of formulating the hydroxy acid with a non-alkali metal base such as ammonium hydroxide or an organic base such as a primary, secondary or tertiary organic amine, thereby forming an amide or ammonium salt of the active ingredient hydroxy (or keto) acid. See U.S. Pat. Nos. 4,105, 782 and 4,105,783 (Yu et al.). The effect of such formulations is, again, to raise the pH of the preparation to a non-irritating level. However, the increased pH (reduced acidity) of the resulting preparations renders them less efficacious as exfoliating or anti-wrinkle agents, which desirably have an acidity equivalent to pH 0.5-6, and more preferably pH 3-5. See Smith, above, at Table 1. Other approaches to reducing the irritation associated with exfoliant products include the use of slow-release topical formulations such as polymer-based vehicles (see, e.g., Chess et al., U.S. Pat. No. 4,971,800) or microsponges, and inclusion of, e.g., plant-derived anti-irritant components (see, e.g., Smith et al., U.S. Pat. No. 5,028, 428).

Mishima, et al. have reported that certain alkali or alkaline-earth metal salts of lactic acid were useful as skin-whitening agents (U.S. Pat. No. 5,262,153), but no recognition is expressed as to any need or ability to reduce irritation effects; in addition, the particular formulations of Mishima were typically "neutralized" or adjusted to pH 5.5 prior to screening or skin-whitening testing (see Experiments 1 and 2).

A clear need exists, therefore, for topical product formulations that reduce or do not result in skin irritation which can be caused by low-pH (high-acidity) organic or inorganic acid ingredients and that retain the efficacy of such acids as exfoliant/cell-renewal agents. More generally, it would be highly desirable to identify topical product formulations that would reduce or prevent the irritation caused by a wide range of otherwise safe and effective topical product ingredients, or to reduce or prevent the intrinsic irritation associated with various skin diseases and conditions (such as atopic dermatitis, eczema or psoriasis) or caused by exposure to irritating chemicals or environmental conditions such as sun, wind or extremes in humidity.

As explained in more detail below in the Detailed Description, the present invention involves the surprising discovery that the inclusion of strontium metal cation in the topical product formulations of the present invention is useful in reducing the incidence and severity of irritation associated with topically applied skin irritants, including irritation caused by various ingredients of the topical product. While the exact mechanism (or mechanisms) of activity of this cation is not known and the invention is not limited to any particular mechanism, it is presently believed that the strontium cation may reduce irritation by interacting with epidermal nerve cells to prevent or counteract the sensation of irritation, and/or by interfering with irritation-inducing components of skin cells that are triggered by exposure to or application of the skin irritant(s). Thus, the cation may alter the ability of epidermal nerve cells to depolarize or repolarize, as for example by blocking or interfering with ion channel or pump operation or by altering the transmembranal action potential, or the cation may interfere with the transmission of nerve impulses from one nerve cell to another (as by suppressing neurotransmitter release). General descriptions of the function of channel proteins are given in B. Hille (ed.), *Ionic Channels of Excitable Membranes*, Sinauer Associates (Sunderland, Mass.: 2d Ed. 1992), and Siemen & Hescheler (eds.), *Nonselective Cation Channels: Pharmacology. Physiology and Biophysics*, Birkhauser Velgag (Basel, Switzerland: 1993). In addition, or alternatively, the strontium cation may act to inhibit or modify the action of skin cell proteases or other irritation-inducing biological molecules (such as eicosanoids or cytokines) that may otherwise be activated by topical application of skin irritants, or may alter "second-messenger" function within sensory cells.

A number of ionic species, and certain metal cations in particular, have been associated with various aspects of nerve cell activity. For example, during the resting (polarized) state of a typical nerve cell, the intracellular concentration of potassium in the nerve axon is high relative to the extracellular potassium concentration, and the intracellular concentration of sodium is low relative to the extracellular sodium concentration. During the process of nerve depolarization, potassium ions flow out of the cell across the membrane, and sodium ions flow into the cell, through pores created by axonal membrane proteins known as "channels". Following depolarization, membranal proteins known as ion "pumps" act to reestablish the resting, polarized state of the cell.

Other metal ions have also been shown to influence nerve function. For example, calcium ($Ca^{2+}$) is carefully regulated in higher eukaryotic organisms and is reported to have many important effects on cellular and neuronal activity. Calcium signaling pathways control many cellular processes, including fertilization, cell growth, transformation, secretion, smooth muscle contraction, sensory perception and neuronal signaling (Berridge, Nature 361(6410), 315-25 (1993)). The wide diversity of cells which display and use intercellular calcium waves and regulate calcium concentrations inside and outside the cell suggests that calcium levels provide a general mechanism by which cells communicate (Sanderson et al., Mol. Cell. Endocrinol. 98(2), 173-87 (1994)).

More particularly, calcium ion is a transducer of depolarization, and flows into the cell through a calcium channel during depolarization, although the amount of current flow varies from cell to cell (Stein, *Nerve and Muscle—Membranes. Cells and Systems*, pp. 33-64 at p. 56 (Plenum Press 1980); Forsen & Kordel, "Calcium in Biological Systems," in *Bioinorganic Chemistry* (Bertini et al., eds.), University Science Books (Mill Valley, Calif.: 1993), pp. 107-166). Several messenger pathways of intracellular calcium signal transduction also exist, such as inositol triphosphate-induced release of intracellular stores of calcium (Tsunoda, Biochim. Biophys. Acta. 1154(2), 105-56 (1993)). Calcium is a critical second messenger in virtually all cell types, and the signals generated by calcium can be single transients or prolonged elevations of intracellular calcium concentrations. Signaling patterns often vary from cell to cell and may contain more complex features such as calcium oscillations. Sub-cellular calcium signals and local concentration changes suggest even a further level of complexity and control of cell function and specialization. Nathanson, Gastroenterology 106(5), 1349-64 (1994).

Calcium also appears to modulate the release of neurotransmitters and, in a variety of cells, elevated calcium levels may result in stimulation of neurotransmitter release in some experimental systems. The divalent cations strontium and barium, while not normally found naturally in the body in physiologically significant amounts, may, by virtue of their atomic resemblance to calcium, similarly stimulate neurotransmitter release, whereas magnesium and manganese cations may have an inhibitory effect in the same system. Calcium is also involved in the postsynaptic action of neurotransmitters, and may also alter the activity of various nerve cell enzymes. Harris et al., J. Pharmacol. Exp. Therap. 195, 488-498 (1975).

Calcium, strontium, barium and certain other divalent cations have also been reported to modulate or block the gating and/or conductance properties of certain ion transporting proteins such as sodium and potassium channels (Shioya et al., Pflugers Arch. 422, 427-435 (1993); Cukierman, Biophys. J. 65, 1168-73 (1993); Marrero & Orkland, Proc. R. Soc. Lond. B. 253, 219-224 (1993)). One mechanism that has been proposed to explain these effects is that the cations may bind to the outer membrane of the nerve cell, thus altering the electric field locally near the membrane (Stein, above, at p. 57); others have proposed models involving specific interactions between the divalent cations and the channel gate and/or pore (Shioya et al., above; Cukierman, above). Alternatively, the cations may regulate the function of many calcium-binding regulatory proteins such as calmodulin or may affect intracellular second messengers such as cyclic nucleotides ("Calcium: Controls and Triggers," in daSilva & Williams (eds.), *The Biological Chemistry of the Elements: The Inorganic Chemistry of Life*, Oxford University Press (New York: 1991), pp. 268-98).

Early studies involving selected nerve cell samples indicated that certain divalent cations, including magnesium and calcium, can have a "depressant" effect on nerve activity (Frankenhaueser & Meves, J. Physiol. 142, 360-365 (1958); Krnjevic, Brit. Med. Bull. 21, 10 (1965); Kato & Somjen, J. Neurobiol. 2, 181-195 (1969); Kelly et al., J. Neurobiol. 2, 197-208 (1969)). These results were generally attributed to post-synaptic membranal effects, as for example the inhibition of potassium or sodium currents in nerve samples exposed to the cations.

While laboratory studies such as these using cultured single cells or microelectrode single-cell electrophysiological techniques have done much to advance the understanding of nerve activity, distinct challenges are presented in the clinical setting. A number of factors make it difficult to predict what effects, if any, particular agents (cationic or otherwise) may have on nerve activity and sensation in intact animal bodies. For example, the animal body (and particularly the human body) contains a wide variety of nerve-containing tissues and organs adapted to perform many different and specialized functions. Other cells in the body—notably muscle cells and neuro-endocrine secretory systems—are "excitable" in a manner akin to nerve cell excitation. In order to achieve the disparate functions required in the animal body, the various tissues and organs are differently disposed within the body, and the nerves (and other excitable cells) within a given tissue are typically highly specialized as well as uniquely disposed within the particular tissue. As a result, different nerve-containing tissues may respond differently to a given agent depending on, for example, the type of nerve (or other excitable) cell and its structural disposition within the tissue, the mode of administration of the agent, the ability of the agent to penetrate to the respective nerve site, and the rate at which the agent is removed from the nerve site.

For example, while certain divalent cations including magnesium and calcium have long been reported in laboratory studies to have a "depressant" effect on nerves, clinical studies have shown that intravenously-administered magnesium sulfate produces neither anesthesia nor even analgesia in humans (Kato et al., Can. Anaes. Soc. J. 15, 539-544 (1968)). Instead, the magnesium ion induces paralysis of skeletal muscles, due perhaps to the inhibitory effects of magnesium on muscle cell activity. Oral ingestion of large doses of magnesium (e.g., magnesium sulfate as a laxative) does not result in paralysis or depressed neural activity in healthy individuals. On the other hand, when magnesium is applied directly to the brains of test animals, depressed neural or synaptic activity, and even a sleep-like state, reportedly result (Kato et al. (1968), above).

In addition, the mechanisms underlying sensory stimulation and perception in the animal body are diverse and exceedingly complex. Even within a single tissue or organ, different nerve groups having different organizations and functions may appear. Depending on how they are disposed within the tissue, the various nerve groups may be differently affected (or affected not at all) by an applied agent. Moreover, to the extent that different types of nerve cells occur within a tissue, they may have different susceptibilities to a particular applied agent. This is particularly true in the skin, which has nerves adapted to sense a wide variety of sensory inputs.

Another complicating factor arises from the detailed nature of nerve cell activity and response. The firing activity of an individual nerve cell may be influenced in a complex fashion, and may vary over time, depending on such factors as the extracellular and intracellular concentration of nerve-related ions as sodium, potassium, chloride, calcium and the like, as well as the time course of exposure to such ions. Other bioactive agents, such as prostaglandins present during inflammatory responses, may further influence nerve sensitivity. In addition, nerves may respond to non-chemical stimuli such as hydrodynamic pressure changes, which in turn may depend on the nature of the tissue in which the nerve is disposed. Such factors lead to considerable clinical uncertainty as to how various agents may affect such nervous responses.

For example, studies have been undertaken over the last several decades in an effort to identify and elucidate the effects of various putative tooth-desensitizing agents and therapies. Tooth nerves are disposed primarily in the central pulp of the tooth, but also extend partially into the surrounding "dentin" material. The dentin material is a mineralized collagen matrix containing microscopic, fluid-filled "dentinal tubules." It has long been known that tooth nerve activity (which is sensed as pain) may be triggered by hydrodynamic pressure changes in the tubule fluid, as may be caused for example by probing or air-blasting the tooth or by applying an ionic solution having a high osmotic pressure (particularly when the protective enamel surrounding the dentin is degraded). Accordingly, one reportedly effective treatment for tooth hypersensitivity involves sealing or occluding the dentinal tubules using chemical or physical means (Scherman & Jacobsen, J. Am. Dent. Ass. 123, 57-61 (1992)). In addition, potassium and strontium salts, particularly potassium nitrate and strontium chloride, have been employed in dentrifices and are reported to reduce tooth sensitivity following two to six weeks of continuous use (Scherman & Jacobsen, above; Silverman, Comp. Cont. Dent. Educ. 6, 131-136 (1985)). One mechanism commonly advanced to explain this putative desensitizing activity is that precipitated potassium or strontium ions block or inhibit fluid flow within the dentinal tubules (Scherman & Jacobsen, above; Knight et al., J. Periodontal Res. 64, 366-373 (1993)). This explanation is consistent with the chemical/physical sealing therapies noted above, and also appears consistent with the clinical observation that several weeks of treatment are required in order to achieve substantial desensitizing effects.

A number of studies have attempted to elucidate other possible effects of various ions on tooth nerve activity, and have established that such effects may vary greatly depending on the clinical or experimental system employed. For example, pain is induced when potassium ion is applied to exposed tooth pulp but not when applied to the dentin (Nahri et al., Arch. Oral Biol. 27, 1053-58 (1982). Hypertonic solutions of calcium and magnesium salts have been reported to evoke pain and/or transient nerve electrical activity when applied to the dentin, probably due to dentinal tubule water movement induced by osmotic pressure effects (Orchardson, in Lisney & Matthew (eds.), *Current Topics in Oral Biology*, University of Bristol Press (Bristol: 1985), pp. 205-215; Nahri, above; Markowitz & Kim, Proc. Finn. Dent. Soc. 88 (Supp. 1), 39-54 (1992)). On the other hand, electrical activity studies undertaken on exposed tooth nerves (obtained, for example, by deeply abrading the dentin material) have indicated that various divalent cations (particularly calcium and magnesium) may suppress nerve electrical responses, while monovalent potassium evokes a transient electrical response followed by inhibition of excitability (Markowitz & Kim, above; Orchardson, above). In the final analysis, the Markowitz and Kim group concluded that it is difficult to explain the clinical desensitizing effects of the available ionic desensitizing dentrifices (which require several weeks of treatment) in terms of a direct nerve cell membrane function, and that studies undertaken with exposed nerves may not reflect the pain-induction mechanisms observed clinically (Markowitz & Kim, above).

The human skin presents a sensory and structural environment that is much more complicated than that of the tooth. For example, the skin contains nerves and highly specific sensory organs that are specialized and disposed so as to differentiate the stimuli leading to such distinct sensations as heat, cold, pressure, pain, itch and the like. In addition to normal sensory stimuli, nerves in the skin are also responsive to native or foreign chemicals such as proteases, prostaglandins, complement-system molecules, allergens, mitogens and the like which may be presented due to tissue injury or environmental exposure. Agents which are effective to combat one source of sensory stimulus—for example steroidal agents to treat skin inflammation—are ineffective against other sensory stimuli such as pressure, heat, or the transitory sting or itch caused by an applied skin care product. Conversely, local anesthetic agents which are effective to depress all sensory or even motor activity in a treated region are not desirable if only a single sensation—for example a transitory sting or itch—is sought to be eliminated. To complicate the situation, the structural matrix of the skin affords a "barrier function" which tends to exclude or inhibit the entry of foreign material, including potentially therapeutic agents.

Accordingly, it is desirable to identify agents which are effective in the skin to inhibit certain identified sensory responses (as for example burn, sting, or itch) while not adversely affecting other nervous responses in the same tissue (as for example tactual sensations), and to include such anti-irritant agents in topical product formulations. In copending application Ser. No. 08/362,100, filed Dec. 21, 1994, from which the present application is a continuation-in-part, we identified strontium cation, and certain aqueous-soluble salts thereof, as effective in suppressing skin irritation due to sources such as chemical and environmental exposure, or tissue inflammation, injury or skin pathology.

Thus, one aspect of the present invention is to provide topical product formulations that comprise strontium cation (or a suitable aqueous-soluble strontium salt) at a concentration effective to reduce irritation to the skin produced by these sources.

Another aspect of the invention is to provide topical product formulations that comprise strontium cation (or a suitable aqueous-soluble strontium salt) to reduce or inhibit skin irritation caused by various other ingredients in the topical product, including the non-strontium active ingredient(s) of the product.

A third aspect of the invention is to provide topical product formulations comprising an aqueous-soluble strontium salt (at concentrations effective to inhibit skin irritation) wherein (i) the formulation is stable at such strontium salt concentrations; (ii) the formulation retains its efficacy and aesthetic qualities at these strontium salt concentrations; and (iii) the active ingredients of the formulation (including the strontium cation) penetrate the stratum corneum of the skin and thus are bioavailable to the living cells of the skin.

SUMMARY OF THE INVENTION

The present invention is directed to topical product formulations containing the divalent cation strontium ($Sr^{2+}$) and aqueous-soluble salts thereof as ingredients to provide fast-acting, efficient: and safe topical skin anti-irritant effects. It is one object of the present invention to provide topical formulations and ingredients which can suppress skin irritation due to chemical or environmental exposure, or due to tissue inflammation, injury or other skin pathology. The invention is particularly useful for preventing, reducing or eliminating the potential irritation caused by topical application of products containing irritating ingredients, including especially cosmetics such as hydroxy acid or other exfoliant containing products, facial peels, shaving products, sunscreen products, deodorants and other cosmetics as described above, as well as topical drug/therapeutic products containing irritating active ingredients or vehicles, and other products such as cleansing products, including soaps, detergents, solvents and the like which are either applied topically or are topically exposed to the body. Thus, the present invention meets a clear need for formulations and ingredients that will prevent or reduce the potential skin irritation caused by topical products. The formulations of the present invention may be topically applied simultaneously with, prior and/or subsequent to application of irritating topical products, such as those described above. Alternatively, such cosmetic, therapeutic, cleansing and other irritating topical products themselves may be formulated to comprise divalent strontium cation, which would act to inhibit or suppress the skin irritating properties of other various ingredients in these formulations.

The invention is also useful for preventing, reducing or eliminating the skin irritation caused by skin diseases or other conditions such as environmental exposure to irritating chemicals or influences such as wind, heat, cold and extremes in humidity, including the intrinsic irritation associated with these conditions as well as such irritation as may be exacerbated by the application of a topical product.

Preferred embodiments of the formulations of the present invention comprise an anti-irritant amount of the strontium cation accompanied (as in the form of a salt) by one or more ionizing anionic species, preferably an acidic anion species such as a chloride, nitrate, or acetate anion, dissolved or dispersed in an appropriate vehicle. Investigations relating to the present invention have shown that the anti-irritant effects of the cations of the invention can be optimized by suitable selection of the accompanying anionic species. Especially preferred cation-anion pairs include strontium chloride, strontium nitrate, and strontium acetate.

In the preferred embodiments, the strontium cation of the invention is included in a suitable topical formulation vehicle at a concentration of about 50 to about 1000 mM, more preferably about 100 to about 500 mM, and most preferably about 150 to about 300 mM. The most highly preferred concentration range in many instances is from about 200 to about 300 mM, as for example where the formulation of the invention includes an irritant ingredient such as an exfoliant ingredient or where the formulation of the invention is applied to the skin immediately prior or subsequent to (or simultaneously with) the topical application of a product containing an irritant ingredient. The appropriate cation concentration can be achieved, for example, using a single strontium salt, or multiple different cation salts may be combined to yield the total desired cation concentration.

In one preferred embodiment, the strontium cation is combined in a topical product formulation further, comprising a potentially irritating ingredient, the cation being present in a total amount effective to reduce or eliminate irritation due to the irritant ingredient.

In another preferred embodiment, the formulation of the invention comprises the strontium cation paired with one or more anionic species selected so as to achieve a desired level of acidity or basicity in the formulated composition, and a total cation concentration effective to reduce skin irritation. In one such particularly preferred embodiment, strontium is combined in a hydroxy acid or other exfoliant preparation accompanied by one or more suitable anionic species such that the pH of the hydroxy acid preparation is maintained in the range of pH 0.5-6, and more preferably in the range of pH 3-5. It will be understood that, where the formulation employs an anhydrous vehicle, the acidity of the formulation may not be expressible in typical pH terms, but that such acidity will manifest itself upon exposure of the formulation to the skin where water is present both intracellularly and extracellularly.

In another embodiment, the formulation of the present invention may comprise strontium cation combined in the formulation with other anti-irritants, such as steroidal or non-steroidal anti-inflammatory agents or other materials such as aloe vera, chamomile, α-bisabolol, cola nitada extract, green tea extract, tea tree oil, licorice extract, allantoin, urea, caffeine or other xanthenes, glycyrrhizic acid and its derivatives, or with other anti-irritant species such as those identified in co-pending patent application Ser. Nos. 08/362,101, 08/362,097, 08/362,055 and 08/362,058 (entitled "Formulations and Methods for Reducing Skin Irritation"), filed on Dec. 21, 1994 and in co-pending patent application Ser. No. 08/384,263 (entitled "Amino Acid Formulations and Methods for Reducing Skin Irritation"), filed on Feb. 3, 1995, by the present inventors, so as to achieve a multiple anti-irritant effect.

The invention further provides formulations for treating, reducing or eliminating skin irritation comprising the topical application of a formulation comprising an anti-irritant effective amount of strontium. The formulation may further include one or more potentially irritating components. Alternatively, the strontium cation formulation of the present invention may be applied separately and prior to application of another product containing a potentially irritating component, or the formulation may be applied alone in order to prevent the development of irritation or to treat a pre-existing irritation attributable to conditions such as skin disease, chemical irritant exposure or environmental exposure.

The invention further provides vehicles and vehicle components that are especially useful in the formulations of the invention, as well as concentration ranges and processing steps to obtain useful formulation forms including solids, creams, lotions, gels, and liquids.

BRIEF DESCRIPTION OF THE DRAWINGS

FIGS. 1 through 4 depict experimental data showing the time course of irritation responses (FIG. 1), the cumulative irritation over time (FIG. 2), and the subject-by-subject cumulative irritation suppression and irritation responses (FIGS. 3 and 4) for a panel of humans treated with 250 mM strontium nitrate (and control) in a lactic acid skin irritation challenge.

DETAILED DESCRIPTION

Figure 3:
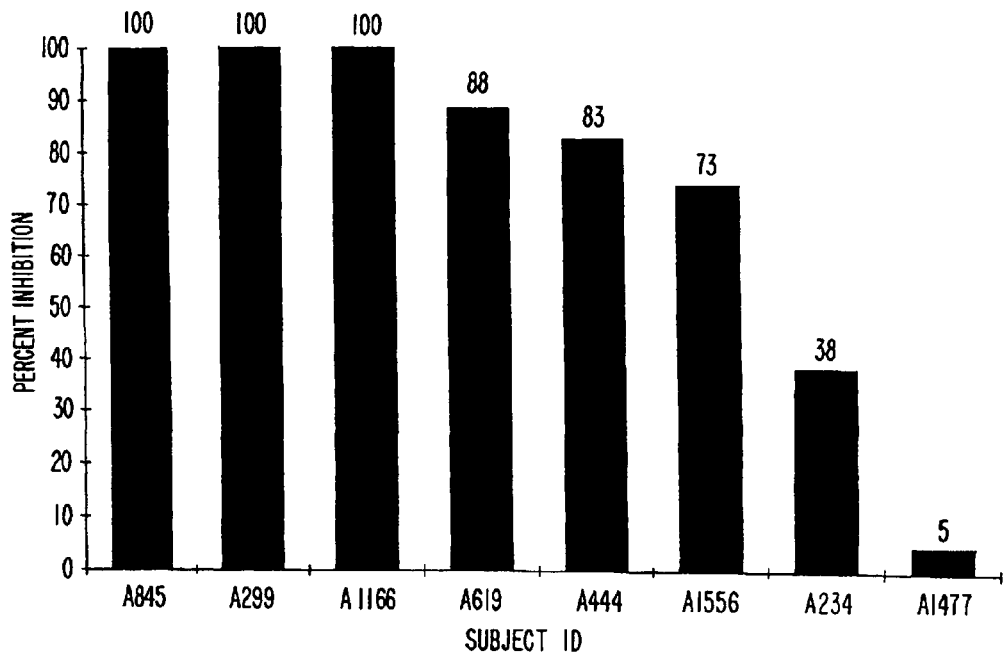

Human clinical trials undertaken in connection with the present invention have established that the cation species strontium(II) ($Sr^{2+}$) is effective, when applied topically to the skin in appropriate concentrations and vehicles, to suppress the relatively severe stinging, burning, tingling, itching and/or erythema induced by topical application of the hydroxy acid skin irritant lactic acid as well as the skin irritants glycolic acid, capsaicin, capryloyl salicylic acid, benzoyl peroxide, and post-shaving-applied seawater, among others. Formulations containing the strontium cation are useful in suppressing a wide range of topical-product-induced irritation responses attributable to exfoliants, sunscreens, retinoids, anti-perspirants, deodorants, anti-acne and other products which contain components potentially capable of causing irritation. For example, the strontium cation has been found to be useful for preventing or reducing the skin irritation caused by α- or β-hydroxy acids, α-keto acids and other carboxylic acids, as well as retinoids, phenols, peroxides and similar irritants found in over-the-counter topical products for home or cosmetologist use such as, 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, and gluconic acid, as well as in certain prescription topical drugs containing high (for example, 12% w/w or even higher) dosage forms of such irritants. The irritation attributable to combinations of such irritating ingredients, such as lactic acid/salicylic acid combinations and hydroxy acid/retinoid combinations, as well as irritation attributable to purified isomeric forms of such ingredients, can also be inhibited by the formulations of the invention.

Additionally, formulations containing the cation are useful in ameliorating irritation in conditions where the skin is inherently hypersensitive to topical products (e.g. dry skin, "winter itch," and other inflammation or injury conditions) and in ameliorating the irritation due to such conditions even in the absence of other applied topical products. The formulations are also useful in treating non-human animal skin irritation, as for example dog or cat irritation and resultant scratching due to fleas or other skin disease or condition.

An additional benefit of the present anti-irritant formulations is that they do not have the undesirable anesthetic side-effects (e.g., numbness) exhibited by Lidocaine and other similar skin local anesthetics. Upon application of a solution of the compound used in the clinical trials described here, subjects typically reported no sensations other than those sensations caused by the vehicle alone, and no lack of normal sensations.

FORMULATIONS OF THE INVENTION

The formulations of the present invention overcome several difficult problems inherent in incorporating high concentrations (greater than about 2% w/w) of aqueous-soluble, charged inorganic salts (e.g., strontium salts) into aesthetic (e.g., pleasant-feeling, elegant, etc.) and functionally active topical products (i.e., products which retain their cosmetic, therapeutic, or other functional characteristics).

Many topical formulations contain chemical emulsions which use surface active ingredients (emulsifiers) to disperse dissimilar chemicals in a particular solvent system. For example, most lipid-like (oily or fatty) or lipophilic ingredients do not uniformly disperse in aqueous solvents unless they are first combined with emulsifiers which form microscopic aqueous soluble micelles that contain a lipid-soluble interior and an aqueous-soluble exterior, resulting in an oil-in-water emulsion. In order to be soluble in aqueous media, a molecule must be polar or charged so as to favorably interact with water molecules which are also polar. Similarly, to dissolve an aqueous-soluble polar or charged ingredient in a largely lipid or oil-based solvent, an emulsifier is typically used which forms stable micelles that contain the aqueous-soluble components in the micelle interior while the exterior of the micelle is lipophilic so that it can dissolve in the lipophilic solvent to form a water-in-oil emulsion. It is well known that such emulsions can be destabilized by the addition of salts or other charged ingredients which can interact with the polar or charged portions of the emulsifier within an emulsion micelle. Emulsion destabilization results in the aqueous and lipophilic ingredients separating into two layers, potentially destroying the commercial value of a topical product. Because the aqueous-soluble strontium cation has two positive charges, it is especially disruptive of emulsion systems compared to ions with only one positive charge (e.g., sodium ions). The concentrations of strontium salts, particularly strontium nitrate, in many of the topical formulations of the present invention that provide an optimum consumer benefit (e.g., anti-irritant properties) are approximately 4-6% w/w (approximately 190-280 mM). In this concentration range many common emulsion systems become unstable and separate into their two phases. The formulations of the invention have overcome the inherent tendency of high salt concentrations in general, and high strontium salt concentrations in particular, to destabilize emulsions.

In addition to destabilizing emulsions, formulations with high salt concentrations often precipitate out other ingredients commonly found in topical product formulations like cosmetics and topical therapeutics. Many factors such as pH, choice of solvent, active ingredients, preservatives, and the number and concentrations of many other ingredients may cause salts to precipitate and form crystals, thus reducing or destroying the value of the product. The process of "salting out" proteins and other aqueous-soluble chemicals is well known in the art to be a problem with solutions containing high salt concentrations. The formulations of the present invention have overcome the inherent tendency of high salt concentrations in general, and high strontium salt concentrations in particular, to precipitate ingredients in topical formulations.

One of the most important aspects of topical products in general, and cosmetic products in particular, is the consumer's perception of the aesthetic qualities of a product. For example, while petrolatum (e.g., Vaseline™) is an excellent "moisturizer" and skin product, it is rarely used alone, especially on the face, because it is greasy, sticky, does not rub easily into the skin and may soil clothing. Consumers highly value products which are aesthetically elegant and have an acceptable tactile feel and performance on their skin. Formulations with high salt concentrations frequently have relatively poor aesthetics due to their unfavorable effects on the other ingredients of the formulation. The formulations of the present invention have overcome the inherent tendency of high salt concentrations in general, and high strontium salt concentrations in particular, to produce aesthetically poor products.

In addition to consumers desiring products with excellent aesthetics, topical products must perform as consumers expect. For example, an alpha hydroxy acid-containing moisturizer or exfoliant must retain its moisturizing or exfoliant properties when formulated into a particular formulation. Similarly, a sunscreen, antiperspirant and acne therapeutic must all produce their intended effect. The formulations of the present invention all preserve the primary activity of the topical product while allowing the anti-irritant activity of the strontium salt to provide consumer benefit.

Another major challenge inherent in formulating topical products designed to deliver a biologically active ingredient to the living skin is to enable the active ingredient to penetrate the stratum corneum and thus be "bioavailable" to the living cells of the skin. The stratum corneum is highly impermeable to many molecules and serves to prevent body fluids from leaking out of the skin and prevents foreign molecules from penetrating into the body. In order for the strontium salts of the present invention to exert their anti-irritant effects, they must penetrate the stratum corneum to a sufficient extent to contact the nerves and other cells responsible for producing cutaneous irritation. Since the stratum corneum is especially impermeable to charged molecules, the challenge of formulating products which deliver sufficient strontium ion through the stratum corneum is a distinct challenge. The formulations of the present invention are optimized to enable strontium ion to be bioavailable to the skin and thus provide the consumer with effective anti-irritant benefits.

The anti-irritant topical formulations of the invention comprise a topical vehicle suitable for administration to the animal (particularly human) skin, and an amount of the strontium cation effective to reduce, inhibit or eliminate existing or potential skin irritation or inflammation. The cation component is, of course, accompanied in the formulation by one or more charge-neutralizing anionic counterions, although the cation-anion pairs as originally incorporated into the vehicle may become dissociated in the resulting formulation, or the strontium cations may become associated in the formulation with other anionic species appearing in the overall formulation. In one embodiment, the anti-irritant topical formulations additionally contain an irritant ingredient(s) that is itself capable of inducing skin irritation or inflammation, as for example a cosmetic or skin care-product ingredient, or a pharmaceutically active ingredient or drug ingredient.

The topical anti-irritant formulation of the invention contains the divalent cation strontium ($Sr^{2+}$) in a concentration effective to prevent or reduce (hereafter, "inhibit") the skin irritation that is sought to be eliminated. The formulation preferably contains this cation component in a suitable topical vehicle at a total concentration of about 50 to about 1000 mM, more preferably about 100 to about 500 mM, and most preferably about 150 to about 300 mM. These preferred concentration ranges correspond to bioavailable forms of such cations within the formulation, particularly, ionizable and aqueous-soluble forms of the strontium cation as contrasted with insoluble or covalently-bonded forms of the cation. If other anti-irritant compounds are included in the formulation, then lower concentrations of the strontium cations may be utilized.

Preferred cation concentrations can also be expressed in weight/volume or weight/weight percentage terms which will vary somewhat depending on the density of the vehicle and other components in the formulation. Thus, to take an example in which the vehicle has a density of 0.93 g/ml (as in a 50:50 [by volume] mixture of 95% ethyl alcohol and water) and the cation component is incorporated in the form of strontium nitrate (formula weight 212), represent molarity concentration values correspond approximately to

| | | |
|---|---|---|
| 10 mM: | 0.21% (w/v) | 0.23% (w/w) |
| 50 mM: | 1.05% (w/v) | 1.14% (w/w) |
| 100 mM: | 2.1% (w/v) | 2.28% (w/w) |
| 250 mM: | 5.3% (w/v) | 5.7% (w/w) |
| 500 mM: | 10.5% (w/v) | 11.4% (w/w) |
| 1000 mM: | 21.2% (w/v) | 22.8% (w/w) |
| 1500 mM: | 31.7% (w/v) | 34.2% (w/w) |

The preferred concentration ranges expressed above contemplate that a typical topical dosage will be approximately 0.5 grams of strontium cation formulation over a 5 cm×5 cm area of skin (25 cm$^2$). Clinical studies have shown that such preferred concentration ranges are generally effective to inhibit skin irritation and, in the formulations of the present invention, do not leave any significant visible residue when applied to the skin. Higher concentration formulations, such as saturated pastes or other forms, may also be successfully used, particularly where visible appearance is not a limiting consideration (as in therapeutic applications).

Furthermore, routine clinical assessments such as those described below can readily be employed to optimize the strontium cation concentration and to ascertain if lower, or higher, concentrations are appropriate for a given formulation or irritation indication. For example, the concentration of strontium cation may be adjusted to account for the amount of formulation that is typically applied to a given skin area by the user, which will depend to an extent on the physical nature of the topical vehicle (e.g., lotion as compared to liquid or cream). Likewise, the amount of cation required may be reduced in such cases where the formulation contains a skin penetration-enhancing ingredient or other agent which increases the ability of the cations to permeate the stratum corneum to their site of anti-irritant activity. Preferably, the formulations of the invention include an amount of anti-irritant cation capable of inhibiting irritation in susceptible individuals by at least about 20% or more, as measured by a mean reduction in cumulative irritation across a susceptible test population as exemplified in the clinical protocols described below. Alternatively, the formulations of the invention include an amount of anti-irritant cation capable of inhibiting irritation by at least about 40% or more in at least about 10% of the susceptible population, as measured by a reduction in cumulative irritation on an individual-by-individual basis (treated vs. control areas). This latter measure of efficacy reflects the fact that the present formulations, similar to many therapeutic products, may in some cases be effective in delivering a significant benefit to some, but not all, of the susceptible population.

The optimum concentration of the strontium cation may also be reduced below (or within) the preferred ranges set forth above if some other anti-irritant component is included in the formulation along with the strontium cation. In particular, it is contemplated that lower (e.g. halved) amounts of strontium ($Sr^{2+}$) cations may be used, while still maintaining comparable levels of anti-irritant activity, by further including an approximately equal concentration of, for example, a potassium channel mediating, regulating or blocking agent, a calcium channel blocking or regulatory agent, or a sodium channel blocking agent, or other anti-irritant agent such as a steroid or non-steroidal anti-inflammatory agent. Examples of suitable additional anti-irritant ingredients are described in applicants' co-pending U.S. patent application Ser. Nos. 08/362,101, 08/362,097, 08/362,055 and 08/362,058 (entitled "Formulations and Methods for Reducing Skin Irritation"), filed Dec. 21, 1994, and co-pending patent application Ser. No. 08/384,263 (entitled "Amino Acid Formulations and Methods for Reducing Skin Irritation"), filed Feb. 3, 1995, and incorporated by reference in their entirety. Other anti-irritant ingredients, such as aloe vera, chamomile, oc-bisabolol, Cola nitida extract, green tea extract, tea tree oil, licorice extract, allantoin, urea, caffeine or other xanthines, and glycyrrhizic acid and its derivatives, may also be beneficially incorporated into the formulations of the invention in order further to inhibit irritation effects or symptoms.

The strontium cation component is typically incorporated into the present formulations by mixing an appropriate amount of a suitable aqueous-soluble salt form of the strontium cation into the chosen formulation vehicle, along with such other skin care components as are desired. From a formulation standpoint, it is preferred that the selected salt be sufficiently soluble in the formulation vehicle as to allow a consistent formulation having the desired physical and topical application characteristics. It will be recognized that, depending on the particular formulation vehicle chosen, the salt form of the strontium cation of the invention may dissociate within the formulation (and in this case may associate with other anions also present in the formulation), or the salt form may remain substantially associated. It is also highly preferred that the salt (or salts) chosen be sufficiently aqueous-soluble such that, upon application to the skin, the component strontium cations (and corresponding counteranions) can dissociate and be
taken up into the water-containing milieu of the skin. In addition, it will be clear that the particular salt ingredient(s) chosen should be topically acceptable and preferably will not themselves be irritating, toxic or otherwise deleterious to the user.

With these considerations in mind, it will be recognized that a variety of topically acceptable strontium/counteranion salt ingredients may be utilized in the present formulations in order to achieve the objectives of the invention. Such salts can be readily identified by those skilled in the art in view of the present disclosure based on known physical (e.g., solubility), pharmacological and toxicological information and, if necessary, by the application of routine experimentation.

Examples of potentially suitable counteranion components for use with the strontium cations of the invention include a variety of mono-, di- and trivalent inorganic and organic anions. Examples of potentially suitable inorganic anions include nitrate and the halogens (particularly Cl, Br and I). Examples of potentially suitable organic anions include carboxylic acids, alkoxylates, amino acids (especially, lysine, arginine, histidine, ornithine, aspartic acid, glutamic acid, proline, and cysteine), peptides, saturated and unsaturated organic acids, and saturated and unsaturated fatty acids. Particular examples include acetate, lactate, glycolate, tartrate, maleate, benzoate, propionate, salicylate, ascorbate, formate, succinate, folinate, aspartate, phthalate, oleate, palmitate, stearate, lauryl sulfate, lanolate, myristate, behenate, caseinate, cyclamate, pantothenate, EDTA and other polyaminopolycarboxylates, saccharin, thioglycolate, laurate, methylparaben, propylparaben, ricinoleate and sorbate anions. It should be recognized that in order for any particular example from the foregoing list of possible candidate counteranions to be suitable for use in the present invention, the corresponding strontium salt must be sufficiently aqueous-soluble. It will also be recognized in view of the foregoing disclosure that certain of these suitable anion components, particularly various carboxylic acid anions, are themselves known active ingredients in various topical products (e.g. exfoliant products), and it will be seen accordingly that such active ingredients anions can be incorporated into useful formulations along with the anti-irritant strontium countercations.

Clinical trials relating to the invention have established that certain cation-anion pairs are particularly active as anti-irritants. These include strontium chloride, strontium nitrate, and strontium acetate.

Also preferred are these and other cation-anion pairs in which the anionic species is acidic, because such pairs will generally exhibit higher solubility in many common topical vehicles and suitable ionization upon application to the skin. In addition, strongly acidic anion components may be useful where it is desired to maintain the pH of the resulting formulation at a relatively acidic level, as for example in the case of hydroxy-acid or other acidic exfoliant products where the activity of the product to exfoliate or reduce wrinkles, or bring about other beneficial effects may be reduced if the formulation is not relatively acidic. In any event, however, the desired level of acidity in such cases can be achieved by adjusting the formulation with a suitable acid (or base if necessary).

In one such particularly preferred embodiment, the strontium cation component is combined in a hydroxy acid or other exfoliant preparation accompanied by one or more suitable anionic or other acidic species such that the pH of the hydroxy acid preparation is maintained in the range of approximately pH 0.5-6, and more preferably in the range of pH 3-5. It will be understood that, where the formulation employs an anhydrous vehicle, the acidity of the formulation may not be expressible in typical pH terms, but that such acidity will manifest itself upon exposure of the formulation to the skin where water is present both intracellularly and extracellularly.

Suitable topical vehicles and vehicle components for use with the formulations of the invention are well known in the cosmetic and pharmaceutical arts, and include such vehicles (or vehicle components) as water; organic solvents such as alcohols (particularly lower alcohols readily capable of evaporating from the skin such as ethanol), glycols (such as propylene glycol, butylene glycol, and glycerin), aliphatic alcohols (such as lanolin); mixtures of water and organic solvents (such as water and alcohol), and mixtures of organic solvents such as alcohol and glycerin (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, demethiconol and dimethicone copolyol (Dow Corning); hydrocarbon-based materials such as petrolatum and squalane; anionic, cationic and amphoteric surfactants and soaps; sustained-release vehicles such as microsponges and polymer matrices; stabilizing and suspending agents; emulsifying agents; and other vehicles and vehicle components that are suitable for administration to the skin, as well as mixtures of topical vehicle components as identified above or otherwise known to the art. The vehicle may further include components adapted to improve the stability or effectiveness of the applied formulation, such as preservatives, antioxidants, skin penetration enhancers, sustained release materials, and the like. Examples of such vehicles and vehicle components are well known in the an and are described in such reference works as *Martindale—The Extra Pharmacopoeia* (Pharmaceutical Press, London 1993) and Martin (ed.), *Remington's Pharmaceutical Sciences*.

The choice of a suitable vehicle will depend on the particular physical form and mode of delivery that the formulation is to achieve. Examples of suitable forms include liquids (e.g., gargles and mouthwashes, including dissolved forms of the strontium cation as well as suspensions, emulsions and the like); solids and semisolids such as gels, foams, pastes, creams, ointments, "sticks" (as in lipsticks or underarm deodorant sticks), powders and the like; formulations containing liposomes or other delivery vesicles; rectal or vaginal suppositories, creams, foams, gels or ointments; and other forms. Typical modes of delivery include application using the fingers; application using a physical applicator such as a cloth, tissue, swab, stick or brush (as achieved for example by soaking the applicator with the formulation just prior to application, or by applying or adhering a prepared applicator already containing the formulation—such as a treated or pre-moistened bandage, wipe, washcloth or stick—to the skin); spraying (including mist, aerosol or foam spraying); dropper application (as for example with ear drops); sprinkling (as with a suitable powder form of the formulation); and soaking.

The topical formulations of the present invention may be prepared in a variety of physical forms. The primary product forms are solids, creams, lotions; gels/serums, and aqueous liquids. The principal differences between these forms are their physical appearance and viscosity (or thickness), which are governed primarily by the presence and amount of emulsifiers and viscosity adjusters; in fact, the main ingredients are, in many cases, common among these product forms. Moreover, a particular topical formulation may often be prepared in a variety of these forms. Solids are generally firm and non-pourable and commonly are formulated as a bar or stick, or in particulate form; solids may be opaque or transparent, and optionally may contain solvents (including water and alcohol), emulsifiers, moisturizers, emollients, fragrances, dyes/colorants, preservatives and active ingredients. Creams and lotions are often similar to one another, differing mainly in their viscosity (creams are typically thicker and more viscous than lotions); both lotions and creams may be opaque, translucent or clear and often contain emulsifiers, solvents (including water and alcohol) and viscosity adjusting agents. Lotions and creams also may optionally contain moisturizers and emollients (especially in the case of skin care products), as well as fragrances, dyes/colorants, preservatives and active ingredients. Gels/serums may be prepared with a range of viscosities, from thick (high viscosity) to thin (low viscosity) and differ principally from lotions and creams in that gels/serums are usually clear rather than opaque. Like lotions and creams, gels/serums often contain emulsifiers, solvents (including water and alcohol) and viscosity adjusters, and may also contain moisturizers and emollients, fragrances, dyes/colorants, preservatives and active ingredients. Aqueous liquids are thinner than creams, lotions or gels, and are generally transparent; liquids usually do not contain emulsifiers. Liquid topical products often contain other solvents in addition to water (including alcohol) and may also contain viscosity adjusters, moisturizers and emollients, fragrances, dyes/colorants/pigments, preservatives and active ingredients.

Suitable emulsifiers for use in the formulations of the present invention include, but are not limited to, Incroquat Behenyl TMS (behentrimonium methosulfate, cetearyl alcohol), non-ionic emulsifiers like polyoxyethylene oleyl ether, PEG-40 stearate, ceteareth-12 (e.g, Eumulgin B-1 manufactured by Henkel), ceteareth-20 (e.g., Eumulgin B-2 manufactured by Henkel), ceteareth-30, Lanette O (manufactured by Henkel; ceteareth alcohol), glyceryl stearate (e.g., Cutina GMS manufactured by Henkel), PEG-100 stearate, Arlacel 165 (glyceryl stearate and PEG-100 stearate), steareth-2 and steareth-20, or combinations/mixtures thereof, as well as cationic emulsifiers like stearamidopropyl dimethylamine and behentrimonium methosulfate, or combinations/mixtures thereof. In addition, cationic emulsifiers are preferably combined or mixed with non-ionic emulsifiers in order to form stable emulsion product forms containing high strontium salt concentrations.

Suitable viscosity adjusting agents (i.e., thickening and thinning agents) for use in the formulations of the present invention include, but are not limited to, protective colloids or non-ionic gums such as hydroxyethylcellulose (e.g., Cellosize HEC QP52,000-H, manufactured by Amerchol), xanthan gum, and sclerotium gum (Amigel 1.0), as well as magnesium aluminum silicate (Veegum Ultra), silica, microcrystalline wax, beeswax, paraffin, and cetyl palmitate. In addition, appropriate combinations or mixtures of these viscosity adjusters may be utilized according to the present invention. A particularly preferred thickening agent for use in the formulations of the present invention, especially in the case of gels/serums, is the nonionic polymer hydroxyethylcellulose, which is compatible with strontium nitrate and is stable at pH values around 3. We have observed stability problems in using Carbopol as a viscosity adjusting agent in low pH strontium salt formulations.

Suitable solvents for use in the formulations of the present invention include, but are not limited to, water, ethanol, butylene glycol, propylene glycol, isopropyl alcohol, isoprene glycol, glycerin, Carbowax 200, Carbowax 400, Carbowax 600, and Carbowax 800. In addition, combinations or mixtures of these solvents may be used according to the present invention.

Suitable surfactants for use in the formulations of the present invention include, but are not limited to, nonionic surfactants like Surfactant 190 (dimethicone copolyol), Polysorbate 20 (Tween 20), Polysorbate 40 (Tween 40), Polysorbate 60 (Tween 60), Polysorbate 80 (Tween 80), lauramide DEA, cocamide DEA, and cocamide MEA, amphoteric surfactants like oleyl betaine and cocamidopropyl betaine (Velvetex BK-35), and cationic surfactants like Phospholipid PTC (Cocamidopropyl phosphatidyl PG-dimonium chloride). Appropriate combinations or mixtures of such surfactants may also be used according to the present invention. Anionic surfactants have been found to present stability difficulties when used alone in formulations containing high strontium salt concentrations. However, we have discovered that anionic surfactants, such as ammonium laureth sulfate (Standapol EA-2), when combined with amphoteric surfactants, such as oleyl betaine and cocamidopropyl betaine (Velvetex BK-35), provide stable formulations even at high strontium salt concentrations. Accordingly, it is particularly preferred to use a combination of anionic and amphoteric surfactants in the formulations of the present invention.

Suitable preservatives for use in the formulations of the present invention include, but are not limited to, anti-microbials such as Germaben II (manufactured by ICI; propylene glycol, diazolidinyl urea, methylparaben, and propylparaben), methylparaben, propylparaben, imidazolidinyl urea, benzyl alcohol, sorbic acid, benzoic acid, sodium benzoate, dichlorobenzyl alcohol, and formaldehyde, as well as physical stabilizers and anti-oxidants such as alpha-tocopherol (vitamin E), sodium ascorbate/ascorbic acid, ascorbyl palmitate and propyl gallate. In addition, combinations or mixtures of these preservatives may also be used in the formulations of the present invention.

Suitable moisturizers for use in the formulations of the present invention include, but are not limited to, lactic acid and other hydroxy acids and their salts, glycerin, propylene glycol, butylene glycol, sodium PCA, Carbowax 200, Carbowax 400, and Carbowax 800. Suitable emollients for use in the formulations of the present invention include, but are not limited to, PPG-15 stearyl ether, lanolin alcohol, lanolin, lanolin derivatives, cholesterol, petrolatum, isostearyl neopentanoate, octyl stearate, mineral oil, isocetyl stearate, Ceraphyl 424 (myristyl myristate), octyl dodecanol, dimethicone (Dow Corning 200-100 cps), phenyl trimethicone (Dow Corning 556), Dow Corning 1401 (cyclomethicone and dimethiconol), and cyclomethicone (Dow Corning 344), and Miglyol 840 (manufactured by Huls; propylene glycol dicaprylate/dicaprate). In addition, appropriate combinations and mixtures of any of these moisturizing agents and emollients may be used in accordance with the present invention.

Suitable active ingredients for use in the formulations of the present invention include, but are not limited to, alpha hydroxy acids, sunscreens, antiperspirants, anti-acne drugs, vitamins (especially vitamins A and C) and minerals, and various prescription and over-the-counter medications. The present invention also contemplates the inclusion of multiple active ingredients within the same topical formulation, and combinations of active ingredients such as those listed above may be used, as appropriate, according to the present invention.

Suitable fragrances and colors, such as FD&C Red No. 40 and FD&C Yellow No. 5, may be used in the formulations of the present invention. Other examples of fragrances and colors suitable for use in topical products are known in the art.

Other suitable additional and adjunct ingredients which may be included in the formulations of the present invention include, but are not limited to, abrasives, absorbents, anti-caking agents, anti-foaming agents, anti-static agents, astringents (e.g., witch hazel, alcohol, and herbal extracts such as chamomile extract), binders/excipients, buffering agents, chelating agents (e.g., Versene EDTA), film forming agents, conditioning agents, opacifying agents, pH adjusters (e.g., citric acid and sodium hydroxide), and protectants. Examples of each of these ingredients, as well as examples of other suitable ingredients in topical product formulations, may be found in publications by The Cosmetic, Toiletry, and Fragrance Association (CTFA). See, e.g., *CTFA Cosmetic Ingredient Handbook,* 2nd edition, eds. John A. Wenninger and G. N. McEwen, Jr. (CTFA, 1992).

Also, a variety of product types, including particularly cosmetics, may be formulated in each of the forms described above (i.e., solids, creams, lotions, gels, and liquids). For example, cleansers (for face and body), shampoos/conditioners, hair treatments/dyes/perms/straighteners, antiperspirants/deodorants, make-up products, and other facial, hand and body products may be formulated in any of the five major product forms: solids, creams, lotions, gels, or liquids. Common solid form products include cosmetics such as lipsticks, blushes and rouges, makeup products, antiperspirant and deodorant sticks, and cleansers such as bar soap and powder detergents. Other examples of solid form products include lozenges and suppositories. Common cream and lotion form products include alpha hydroxy acid (AHA) products, moisturizing products and sunscreens, shampoos/conditioners and other hair care products, and cosmetics like concealers and foundations. Common gel products include shaving gels and aftershaves. Common liquid form products include anti-acne solutions, perfumes/colognes, aftershaves, gargles/mouthwashes, and toners/bracers/skin conditioners.

Other methodologies and materials for preparing formulations in a variety of forms are also described in Anthony L. L. Hunting (ed.), "A Formulary of Cosmetic Preparations (Vol. 2)—Creams, Lotions and Milks," Micelle Press (England, N.J. 1993). See, for example, Chapter 7, pp. 5-14 (oils and gels); Chapter 8, pp. 15-98 (bases and emulsions); Chapter 9, pp. 101-120 ("all-purpose products"); Chapter 10, pp. 121-184 (cleansing masks, creams, lotions); Chapter 11, pp. 185-208 (foundation, vanishing and day creams); Chapter 12, pp. 209-254 (emollients); Chapter 13, pp. 297-324 (facial treatment products); Chapter 14, pp. 325-380 (hand products); Chapter 15, pp. 381-460 (body and skin creams and lotions); and Chapter 16, pp. 461-484 (baby products); the contents of which are incorporated herein by reference.

One aspect of the present invention is to provide formulations containing both strontium cation anti-irritant and an alpha hydroxy acid (AHA). One preferred embodiment employs a formulation whose pH is adjusted to approximately 3.2 in order to maximize the exfoliating activity of the lactic acid while maintaining the anti-irritancy properties of the strontium cation. Another preferred embodiment employs a formulation whose pH is adjusted to approximately 4.5 in order to minimize the exfoliating activity while preserving the moisturizing activity of the lactic acid. Additionally, AHA/strontium formulations may optionally contain moisturizing agents, such as butylene glycol. For example, moisturizing properties may be derived from the combination of butylene glycol and the small amounts of lactate salt which is formed at a pH around 3; this combination optimizes moisturization while not being sticky or tacky on the skin.

The formulations of the invention are most preferably formulated such that the strontium cation component of the formulation (as occurring with any accompanying anion counterion components) is substantially invisible upon application to the skin. This is particularly true in the case of many cosmetic formulations that are applied to the face or other exposed parts of the body, although it is also generally desirable that the cation (and anion) component not be visible even if applied to non-exposed portions of the body. It will be recognized that in some cases, particularly with colored facial skin care products such as blushes, blemish covers, lipsticks and the like, the formulation will be designed to be visible on the skin; in such cases, it is desirable that the cation component not adversely change the appearance or skin feel of the overall formulation as applied to the skin.

In this regard, clinical studies relating to the invention have shown that anti-irritant effects can be achieved using strontium cation concentrations well below those concentrations that, as applied in a typical topical vehicle, result in a visible cation (or salt) residue on the skin. For example; a blended formulation of 500 mM strontium nitrate in a silicone-based vehicle (Dow Corning cyclomethicone [DC344]: cyclomethicone/dimethiconol [DC1401]: cyclomethicone/dimethicone polyol [DC3225C]: water; 10:20:15:55) results in an opaque white lotion which typically leaves no visible residue when applied to the skin of a representative subject.

In another embodiment of the invention, the anti-irritant strontium cation can be formulated into a form for topical oral administration to treat irritation in the mouth or throat such as that due to irritated throats, gum irritation or inflammation or the like, including such irritation as may be exacerbated by spicy or acidic foods. Preliminary studies related to the invention have suggested that oral formulations containing strontium cation in a concentration comparable to that described for external topical application are effective in reducing sore throat irritation. Thus, suitable forms for oral administration include liquids (e.g. mouthwash or gargle solutions) and lozenges. As with other topical forms described herein, the components used in such oral formulations (including the strontium cation salts) should be chosen to be non-toxic. Methods for preparing oral formulations suitable for use in the present invention are well known in the art.

Clinical Results

The anti-irritant efficacy of the formulations of the present invention was tested and confirmed in numerous clinical trials, the results of which are described in the examples below. While these examples further illustrate various aspects and preferred embodiments of the invention as described herein, they are examples only, and should not be considered as limiting the scope of the invention as set forth in the claims.

Example 1

Clinical Studies of Anti-Irritation Activity

The objective of the clinical trials was to determine whether and to what extent topical formulations of the strontium cation reduced or prevented skin irritation caused by certain severe skin irritants, including particularly lactic acid and glycolic acid (which are hydroxy acids), capryloyl salicylic acid (a β-hydroxy acid ester) and capsaicin (an isolate from cayenne and paprika known for its skin-irritating properties). The trials were conducted in a double blind, randomized, vehicle-controlled manner. Various formulations of the invention were tested in over 740 people. The results confirm the highly reproducible anti-irritant activity of the formulations of the present invention.

a. Lactic Acid Irritation Trials

1. Protocol

The majority of the trials were conducted using lactic acid as the skin irritant, and proceeded generally as follows.

The subjects were women who had been screened and shown to exhibit normal to above normal susceptibility to irritation by the tested irritant. Tests were conducted in multiple panels of from 7 to 12 subjects each. Subjects were instructed not to wear any makeup or facial lotions to the clinic the day of testing. The subjects were instructed to wash their face with Ivory bar soap in the clinic prior to application of test solutions.

Lactic acid skin-irritant compositions were formulated in an appropriate vehicle prior to application to the skin of the subjects. In the majority of the tests, the irritant composition was 7.5% lactic acid dissolved in a 10% ethanol-in-water solution.

Test anti-irritant formulations containing measured amounts of strontium salts (concentration 250 mM) were applied either (a) 15 minutes prior to application to the skin of the skin-irritant ("pretreatment test") or (B) simultaneously with the application of the skin-irritant ("time zero test"). In the case of the time zero tests, the anti-irritant formulation included both the lactic acid irritant and the cation anti-irritant ingredient of the invention, whereas in the pretreatment tests the anti-irritant formulation was separately formulated (typically in Elizabeth Arden "Visible Difference Refining Toner," a commercially available alcohol-based cosmetic solution) and applied 15 minutes before application of the irritant composition. Controls were performed by applying corresponding formulation(s) (pretreatment and/or skin-irritant composition) with an equimolar amount of sodium chloride to a contralateral portion of the subject's skin. Typically, the test materials were applied to the face of the subject.

All test solutions (including controls) were applied in a double blind, randomized fashion using the prepared solutions as previously placed in coded vial designated for use on either the right or left side of the face (or other test area). Solutions Were typically applied using a cotton swab (six strokes) or sponge applicator to the face and cheek area extending from the midline of the nose over to the center of the cheek and from the cheek bone down to the jaw line. Application was made first to the right side and then to the left.

Sensory assessment scores were recorded for each treated side of the subject's skin every minute for 15 minutes or until three consecutive scores of "zero" irritation were obtained. The following scaled scores were used for sensory assessment:

| Score | Description of Irritation |
|---|---|
| 0 | NO irritation |
| 1 | SLIGHT irritation -- (Barely perceptible stinging, burning or itching) |
| 2 | MILD irritation -- (Definite stinging, burning or itching) |
| 3 | MODERATE irritation -- (Distinctly uncomfortable stinging, burning or itching; constantly aware of irritation) |
| 4 | SEVERE irritation -- (Continuous stinging, burning or itching, and intensely uncomfortable; would interfere with daily routine) |

Symptom scores were cumulated, separately for the cation-treated and control-treated areas, for each individual and also for the panel as a whole. Individuals not reporting a cumulative score of at least "7" on at least one treatment area were excluded (in a blinded fashion) from further analysis in order to ascertain anti-irritant efficacy with respect to the more severely-susceptible test subjects. From a practical standpoint, scores of "0" and "1" on the above scale would be considered highly desirable for a commercial product because such a response would likely not result in a consumer ceasing to use a product. Some consumers, in fact, might view the "barely perceptible" sensations represented by a score of 1 to be an indication that a facial treatment skin care product (especially an exfoliant) was working as advertised. By contrast, irritation scores of "2", "3" and "4" would likely often result in a consumer never purchasing the product again.

In those subjects and skin samples where an irritation was sensed, the irritation commonly involved a spectrum of burn-sting-itch reactions over time. For example, a subject might at first experience a sting, but moments later might experience an itch with no sting. Subjects experiencing higher levels of irritation (e.g. scores of "3" or "4") occasionally exhibited erythema (visually observable inflammation) in addition to sensory irritation effects.

2. Results

Clinical tests of over 740 subjects, performed as generally described above, demonstrated that the strontium cation has significant and reproducible anti-irritant effects, particularly if administered simultaneously with an irritant compound. The average inhibition of cumulative irritation for various cation salts of the invention (at 250 mM) are shown in the following tables.

Time Zero Tests

| Cation Salt | Percent Inhibition |
|---|---|
| Strontium chloride | 60% |
| Strontium nitrate | 65% |

Pretreatment Tests

| Cation Salt | Percent Inhibition |
|---|---|
| Strontium chloride | 25% |
| Strontium nitrate | 50% |
| Strontium acetate | 46% |

A representative set of test results from several subject panels, performed using cation concentrations of 250 mM, is set forth in the following tables.

Pretreatment Tests

| Cation | Anion | Salt Formula | Vehicle | Percent Inhibition |
|---|---|---|---|---|
| Strontium | Chloride | $SrCl_2$ | VIS DIFFERENCE | 20 |
| Strontium | Nitrate | $Sr(NO_3)_2$ | VIS DIFFERENCE | 56 |
| Strontium | Acetate | $Sr(CH_3CO_2)_2$ | VIS DIFFERENCE | 46 |

Time Zero Tests

| Cation | Anion | Salt Formula | Vehicle | Percent Inhibition |
|---|---|---|---|---|
| Strontium | Chloride | $SrCl_2$ | 10% EtOH | 58 |
| Strontium | Nitrate | $Sr(NO_3)_2$ | 10% EtOH | 64 |

Figure 4:
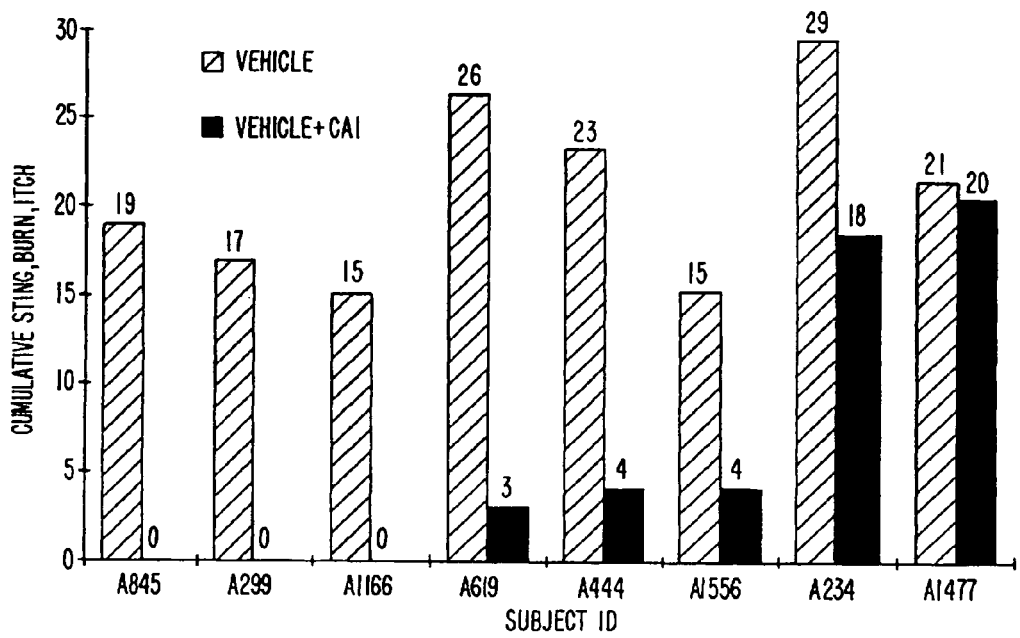

FIGS. 1 through 4 show more detailed experimental data for one panel test conducted using strontium nitrate (250 mM) as the anti-irritant salt component of the subject formulation (time zero test). FIG. 1 shows the time course of irritation responses for both cation-treated and non-treated (control) skin portions for the panel. FIG. 2 shows the cumulative irritation over time for the same panel, while FIGS. 3 and 4 show cumulative irritation suppression and treated/untreated irritation responses on a subject-by-subject basis. While individual responses vary somewhat, the overall efficacy of the subject formulation is clear.

b. Capsaicin Irritation Trials

Similar clinical trials were conducted to assess the efficacy of the cation of the invention to inhibit irritation induced by capsaicin. The clinical protocol was similar to that conducted with lactic acid, with the irritant/anti-irritant and control formulations being applied to the arms of the test subjects. The test compounds of the invention were formulated in Elizabeth Arden "Visible Difference Refining Toner", with the Toner mixed with equimolar sodium chloride serving as the control. The test solutions (and control) were provided in coded vials for application to either the right or left arms. A template (1.5 in.×4.0 in.) was placed on each forearm to mark the challenge area. The pre-treatment solutions containing the anti-irritant cation of the invention were applied to extend 1 inch beyond the marked challenge area in all directions and were allowed to dry for 5 minutes. 0.5 ml of 0.15% capsaicin cream or a swab moistened with capsaicin solution was thereafter applied to each arm by the clinical technician, who rubbed in the cream using gloved fingers. Application and scoring of test and control formulations was performed sequentially for each arm. Scoring was recorded every minute starting at 5 minutes post-application for 10 minutes and then every 5 minutes for 15 minutes (30 minutes total) for the cream, and every minute starting immediately for 15 minutes for the solution. Assessment was made using the irritation scale described above for the lactic acid test, and a simultaneous visual assessment of erythema was made by the monitoring technician.

Figure 5:
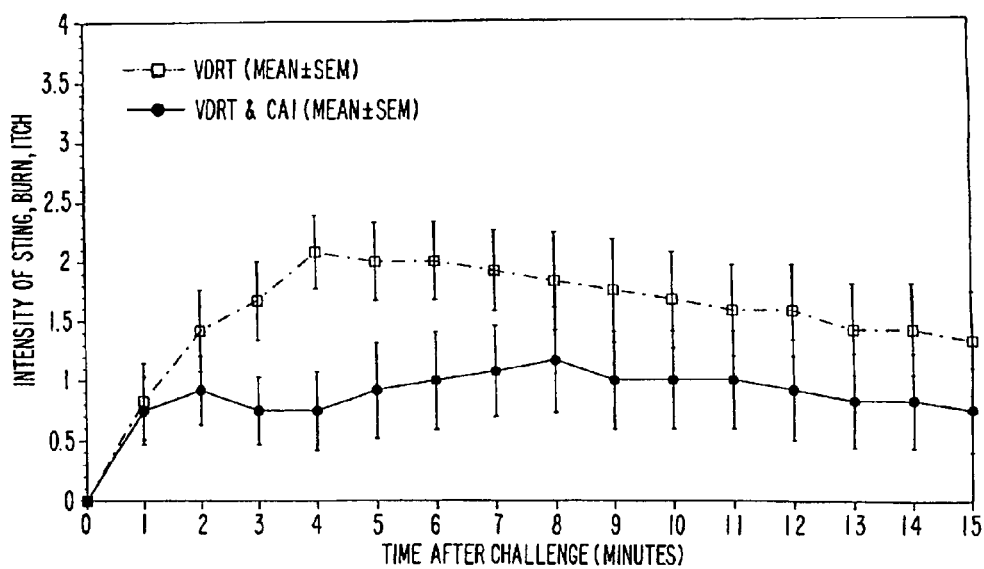
FIGS. 5 through 8 depict experimental data showing the time course of irritation responses (FIG. 5), the cumulative irritation over time (FIG. 6), and the subject-by-subject cumulative irritation suppression and irritation responses (FIGS. 7 and 8) for a panel of humans treated with 250 mM strontium nitrate (and control) in a capsaicin skin irritation challenge.
Figure 6:
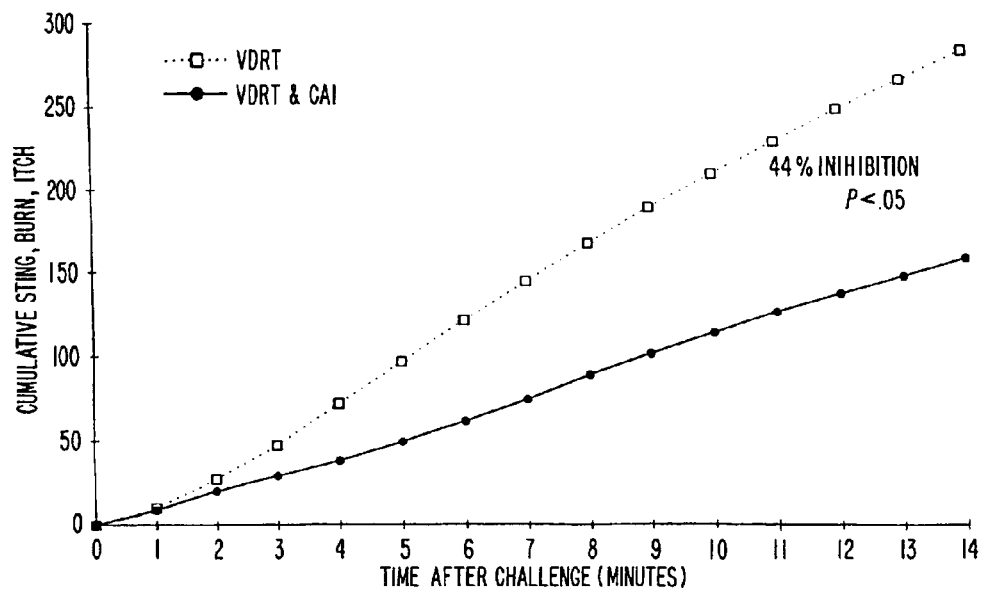
Figure 7:
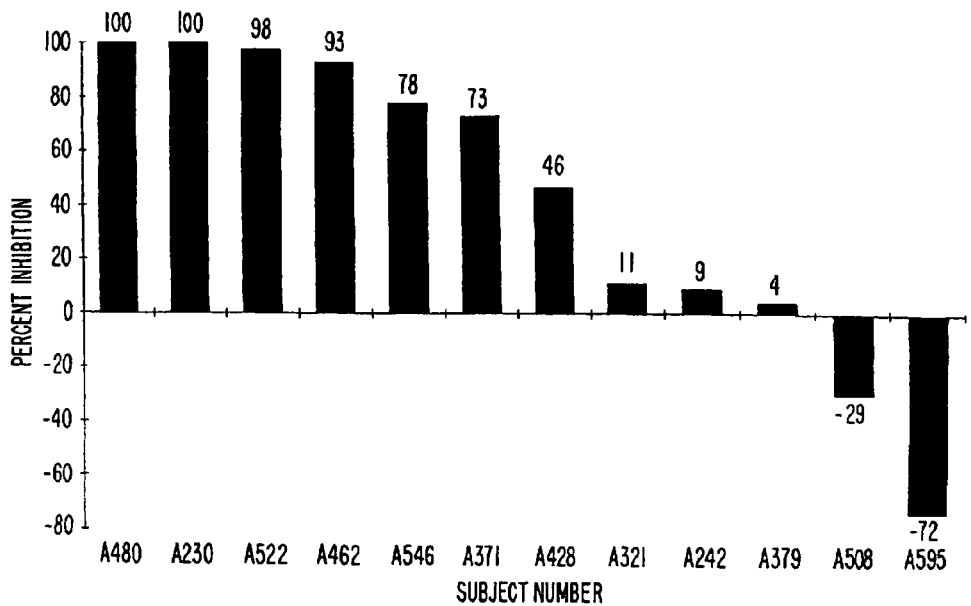
Figure 8:
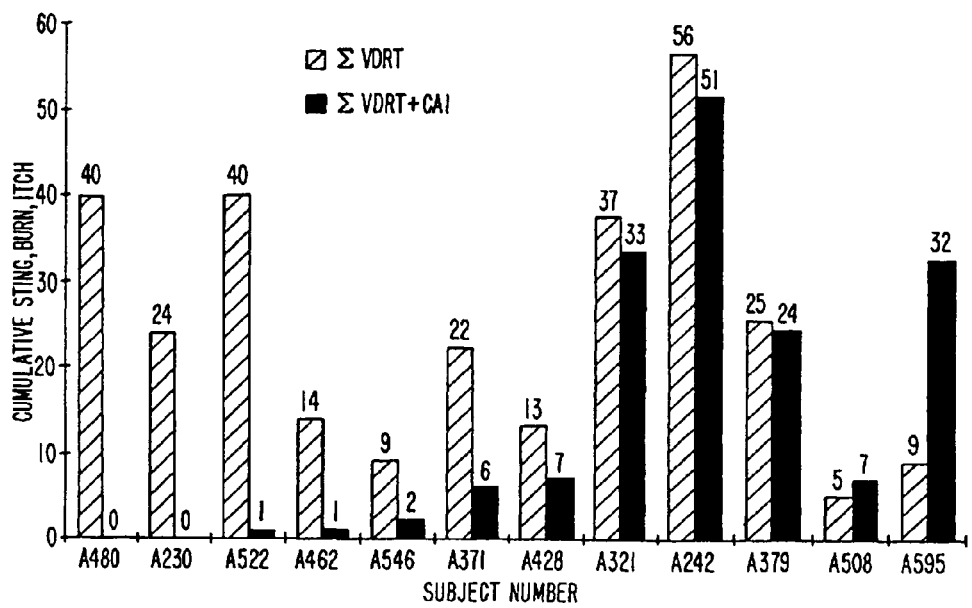
Figure 9:
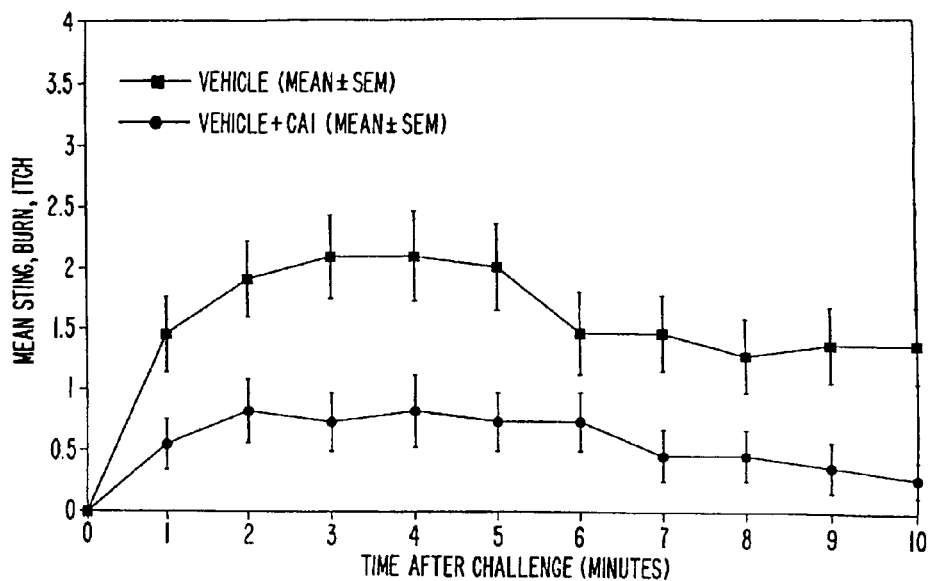
FIGS. 9 through 12 depict experimental data showing the time course of irritation responses (FIG. 9), the cumulative irritation over time (FIG. 10), and the subject-by-subject cumulative irritation suppression and irritation responses (FIGS. 11 and 12) for a panel of humans treated with 250 mM strontium nitrate (and control) in a glycolic acid skin irritation challenge.
Figure 10:
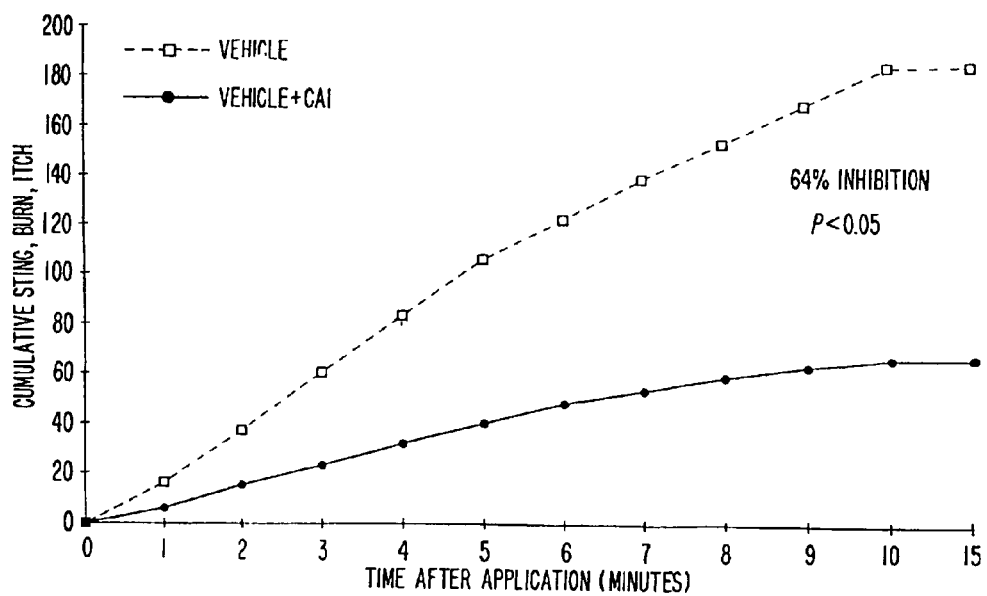
Figure 11:
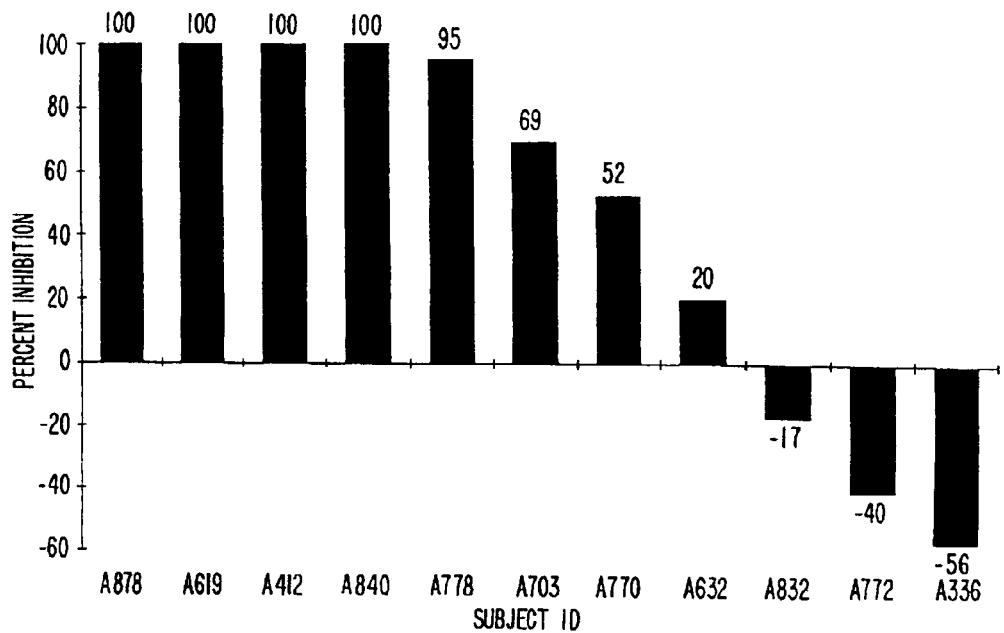
Figure 12:
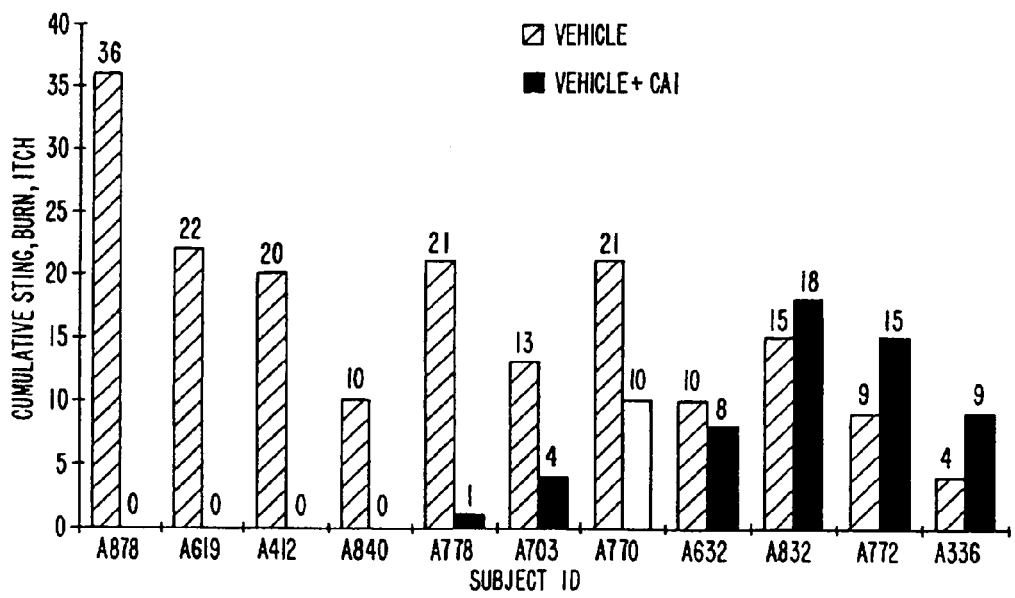

FIGS. 5 through 8 depict results from one representative panel tested in this trial, in which the anti-irritant cation component was applied in the form of strontium nitrate (250 mM). FIG. 5 shows the time course of irritation responses for both cation-treated and non-treated (control) skin portions for the panel. FIG. 6 shows the cumulative irritation over time for the same panel, while FIGS. 7 and 8 show cumulative irritation suppression and treated/untreated irritation responses on a subject-by-subject basis. Here again, while individual responses vary somewhat, the overall efficacy of the subject formulation is evident.

c. Glycolic Acid Irritation Trials

Following a protocol parallel to that of the lactic acid irritant trials described above, glycolic acid (6.0% in 10% ethanol-in-water) was applied as a skin irritant to subject panels. Strontium nitrate was co-administered is an anti-irritant (time zero testing), and was shown to inhibit cumulative irritation in subject panels by 64% to 84% at concentrations ranging from 250 mM to 500 mM. Time course and subject-by-subject data for one such test (cation concentration 250 mM) are presented in FIGS. 9 through 12.

d. Benzoyl Peroxide Irritation Trials

In this test, male and female subjects were recruited who had experienced a grade "2" or higher response in the sting/burn/itch lactic acid irritation protocol described above. Test subjects were limited to those who self-reported a sensitivity (sting, burn, itch) to benzoyl peroxide.

Subjects were instructed not to wear makeup or facial lotions on the day of testing. Those who had applied sunscreens to the face within 24 hours prior to testing, or who had taken any oral analgesic within 12 hours prior to testing, were disqualified. Subjects were instructed to wash their face with Ivory bar soap prior to application of test and control solutions. All materials were applied and scored in a double-blind, randomized fashion.

Facial irritation was induced by application of a 10% benzoyl peroxide wash product ("Oxy 10") to one side of the face. The other side of the face was treated with the same irritant composition containing 250 mM strontium nitrate as the test anti-irritant. Inactive ingredients in the benzoyl peroxide product included citric acid, cocamidopropyl betaine, diazolidinyl urea, methylparaben, propylparaben, sodium citrate, sodium cocoyl isethionate, sodium lauroyl sarcosinate, water, and xanthan gum.

The respective formulations were applied (from coded weighing vessels) using gloved fingers to the cheek area, first to the right side and immediately thereafter to the left. In order to maximize the irritation response above a baseline noise level, the solutions were left on the face for the entire 10 minutes of the study, rather than for only 1-2 minutes as instructed for the commercial benzoyl peroxide product.

To allow for adequate quantitation of the relatively low irritation levels in small numbers of subjects to be measured reliably and true differences in irritation to be determined, a differential scoring scale was developed. Using this method, each subject was asked to rate the magnitude of the difference in irritation response between the two sides of the face, as follows:

| Score | Relative Subjective Irritation |
|---|---|
| 0 | No irritation on either side of face, or No difference in irritation between the right and left sides of face. |
| 1 | Slight difference in irritation between right and left sides of face; difference is barely noticeable and only evident after thinking about it. |
| 2 | Clear difference in irritation between right and left sides of face; difference is obvious and immediately evident. |

It was found that this simultaneous, differential scoring approach allowed for accurate comparisons to be made for the low levels of irritation associated with the present protocol, since it was much easier for the subjects to quantify the difference in irritation when both sides of the face were challenged simultaneously than to rate irritation sequentially on an "absolute" 0-4 scale as used in the lactic acid and glycolic acid protocols. On the other hand, when high levels of irritation are present, the use of sequential "absolute" scoring is preferred because it avoids uncertainty and "carry-over" effects from one side of the face to the other.

Figure 13:
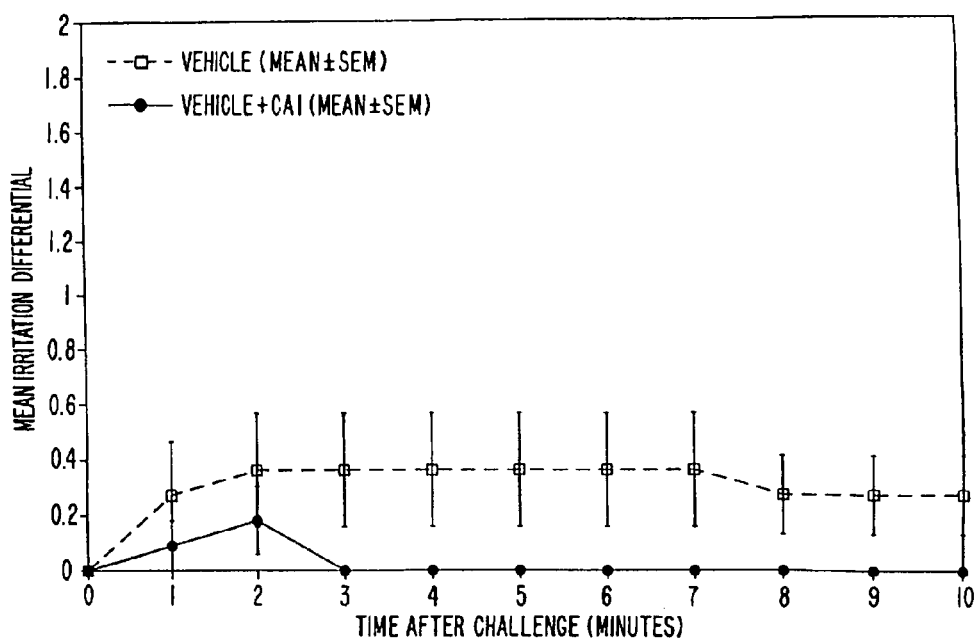
FIGS. 13 through 16 depict experimental data showing the time course of irritation differential responses (FIG. 13), the cumulative irritation differential over time (FIG. 14), and the subject-by-subject cumulative suppression of irritation differential and irritation differential responses (FIGS. 15 and 16) for a panel of humans treated with 250 mM strontium nitrate (and control) in a benzoyl peroxide skin irritation challenge.
Figure 14:
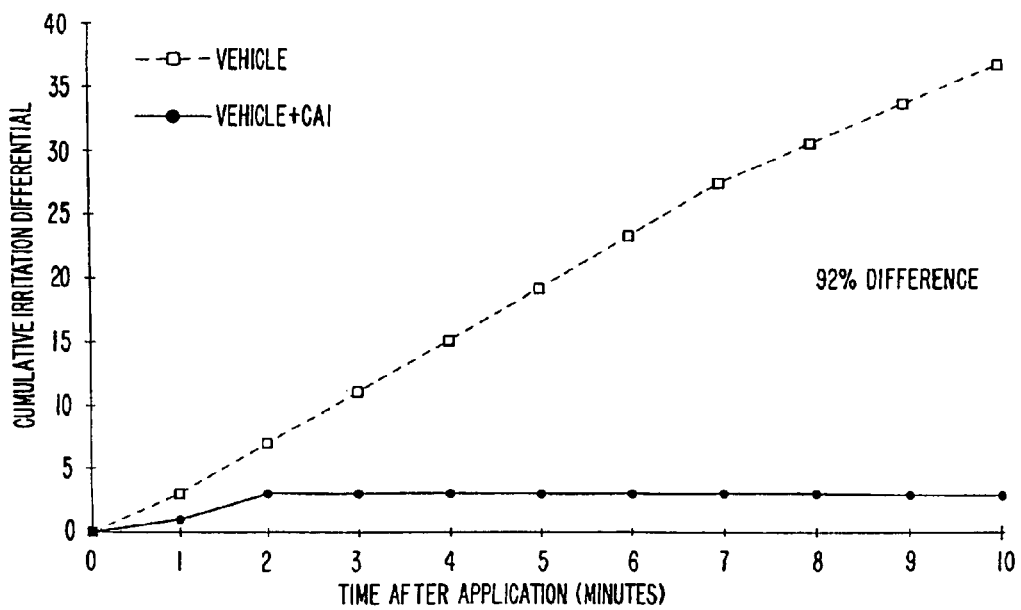
Figure 15:
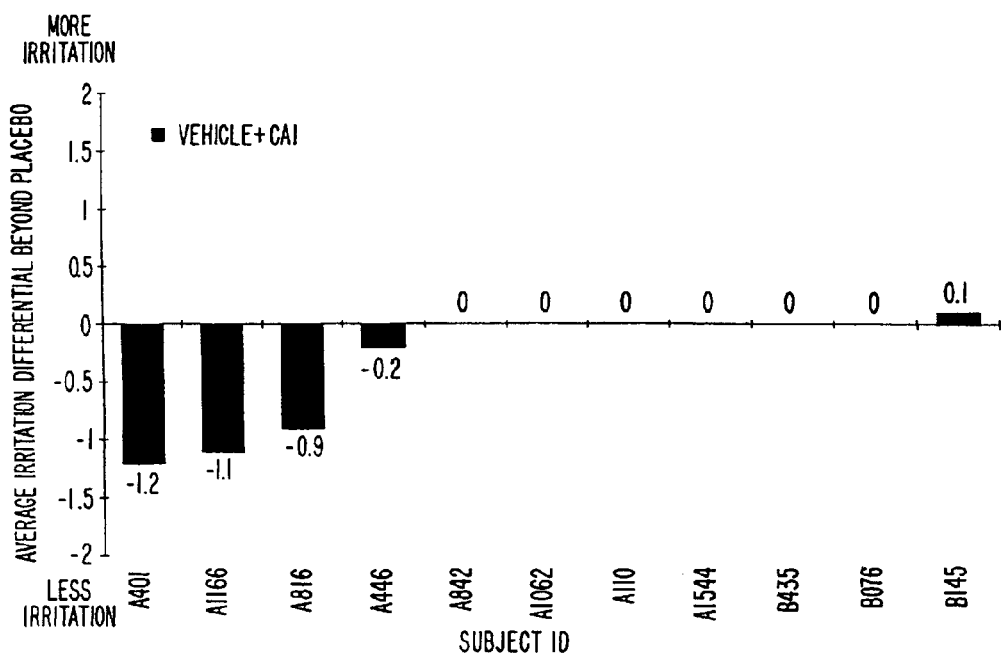
Figure 16:
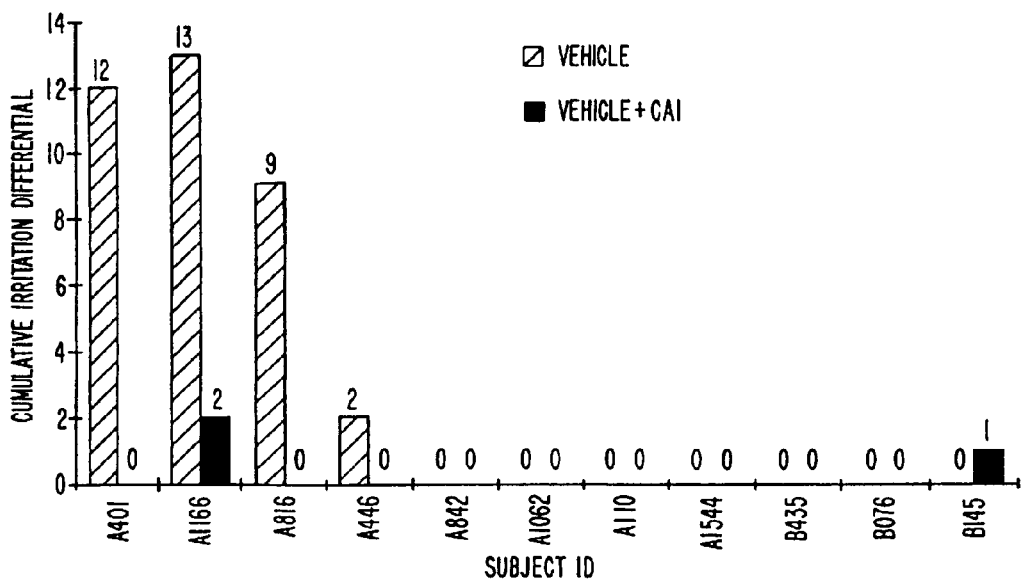

FIGS. 13 through 16 depict results obtained in this protocol using strontium nitrate as the anti-irritant cation component (250 mM). FIG. 13 shows the time course of differential irritation responses for both cation-treated and non-treated (control) skin portions for the panel. FIG. 14 shows the cumulative irritation over time for the same panel, while FIGS. 15 and 16 show cumulative irritation suppression and treated/untreated irritation responses on a subject-by-subject basis.

e. Post-Shaving Ocean Water Irritation

Ocean water is known to induce irritation in subjects with sensitive skin, particularly if the skin has been abraded by shaving or other means. The present test was performed to determine the ability of the present cation formulations to inhibit irritation of shaved skin due to ocean water.

Female subjects were instructed not to apply any sunscreen to their legs within 24 hours prior to testing, and not to ingest any oral analgesic medications within 12 hours prior to testing. The subjects were instructed to shave the lateral portions of their calves, spanning from the ankle to below the knee, with Ivory soap and a disposable razor prior to application of test, control and ocean water irritant solutions. All materials were applied and scored in a double-blind, randomized fashion.

Following shaving, 1 ml of pretreatment solution (test or control) was applied from coded vials to the respective right and left calves using cosmetic sponges. The test cation solution contained strontium nitrate (500 mM) in nanopure water (pH 4.5), and the control vehicle was nanopure water (pH 5.5). The solutions were allowed to dry for 2-3 minutes. Cosmetic sponges saturated with ocean water (La Jolla, Calif.) were used to apply ocean water challenge solutions to the right and left calves within the pretreated areas. The subjects were asked to rate levels of irritation (sting, burn or itch) on right and left calves, and irritation scores were recorded every minute for 10 minutes. The 0-4 scoring scale described above for the lactic acid irritation protocol was used in this test.

Figure 17:
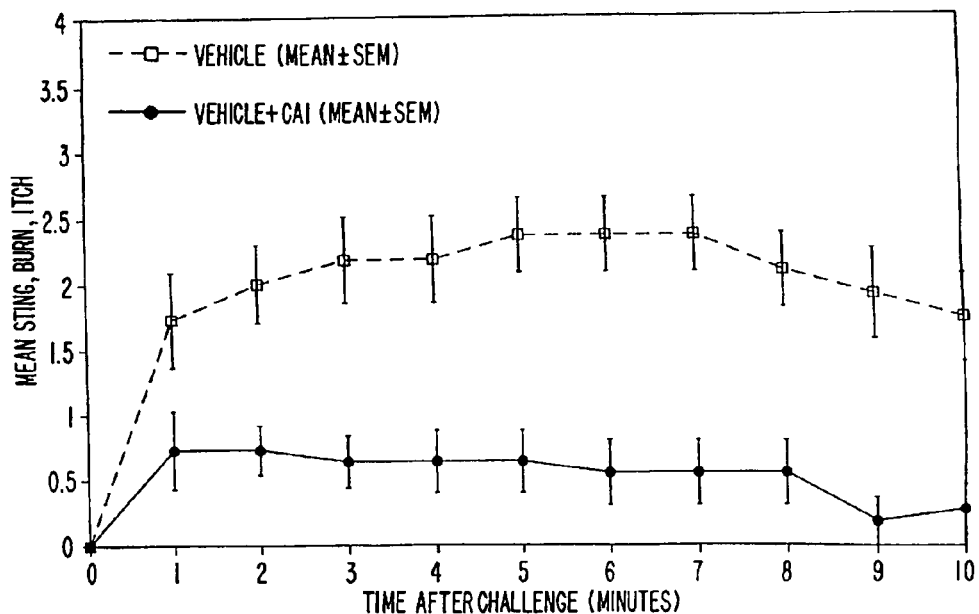
FIGS. 17 through 20 depict experimental data showing the time course of irritation responses (FIG. 17), the cumulative irritation over time (FIG. 18), and the subject-by-subject cumulative irritation suppression and irritation responses (FIGS. 19 and 20) for a panel of humans treated with 500 mM strontium nitrate (and control) in a post-shaving ocean water skin irritation challenge.
Figure 18:
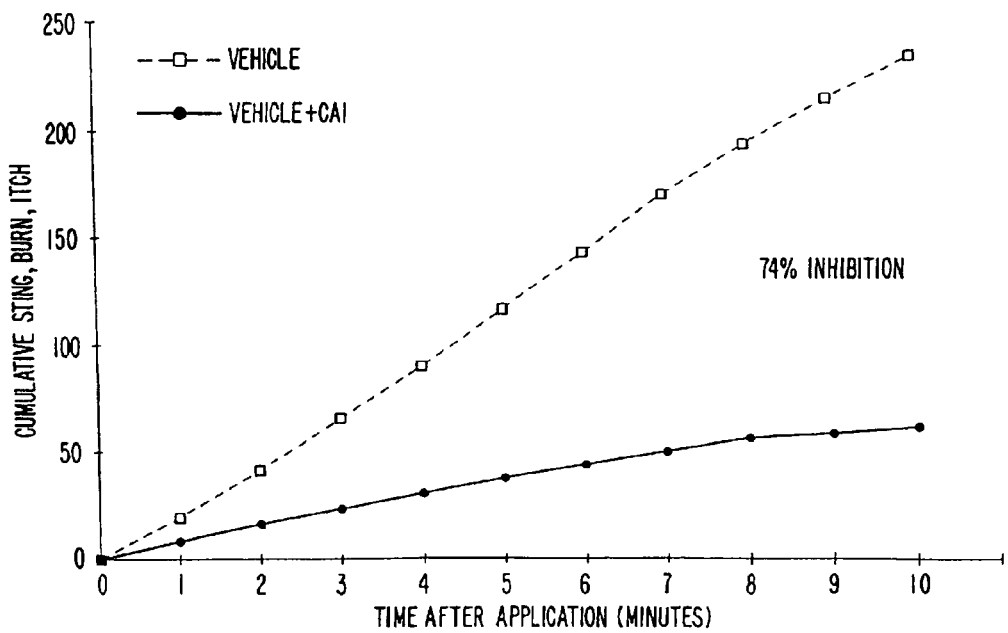
Figure 19:
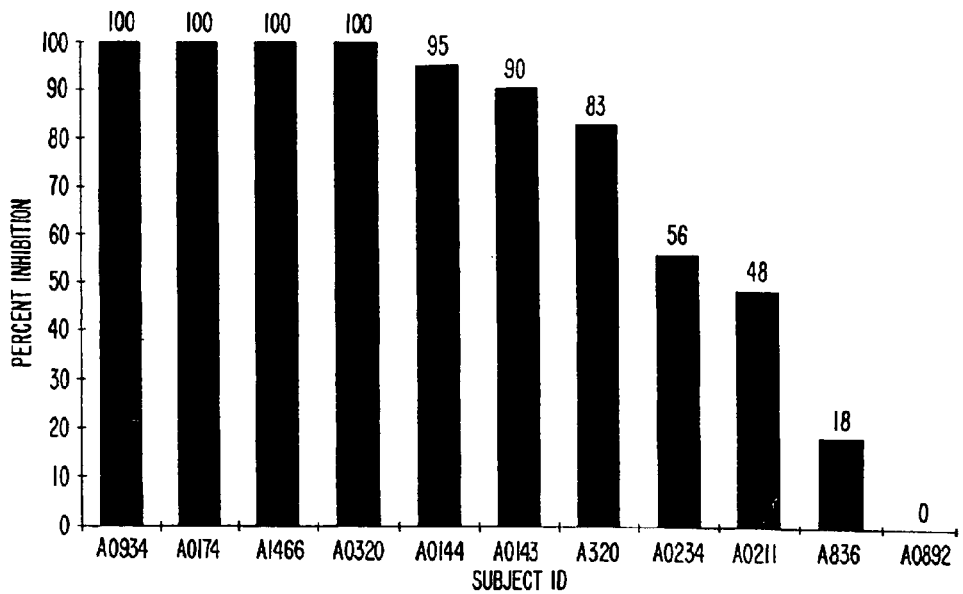
Figure 20:
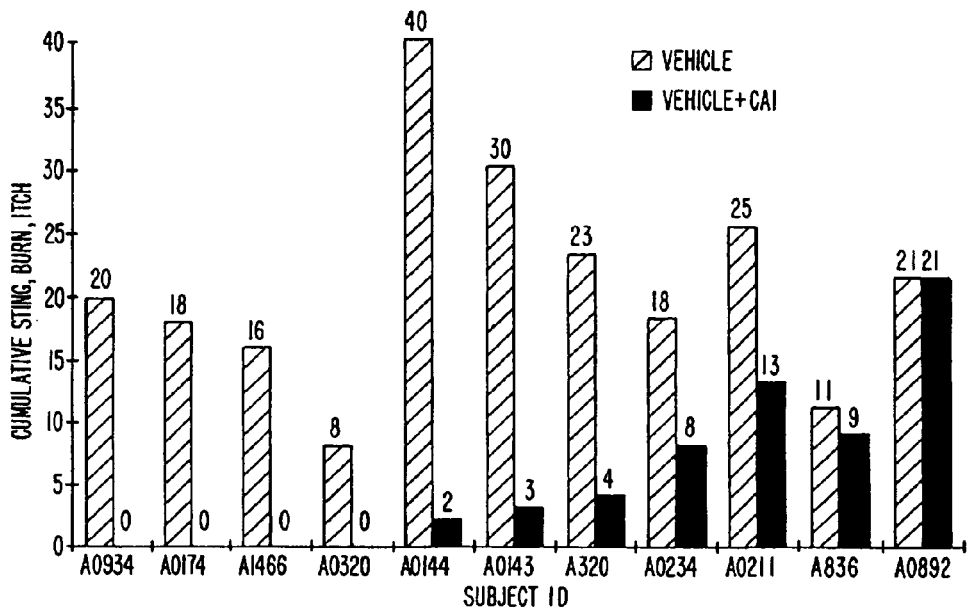

Irritation scores were cumulated for each individual and for the panel as a whole. FIG. 17 shows the time course of differential irritation responses for both cation-treated and non-treated (control) skin portions for the panel. FIG. 18 shows the cumulative irritation over time for the same panel, while FIGS. 19 and 20 snow cumulative irritation suppression and treated/untreated irritation responses on a subject-by-subject basis.

f. Post-Shaving Lactic Acid Irritation

Following a protocol parallel to that of the post-shaving ocean water irritation test described above, a commercial lotion containing 5% lactic acid was applied to contralateral shaved calves of the subject females. The control solution was Vaseline Smooth Legs and Feet Lotion (containing, water, lactic acid (5%), glycerin, isopropyl palmitate, PEG-40 stearate, cetyl alcohol, potassium hydroxide, steareth-2, magnesium aluminum silicate, lecithin, soya sterol, tocopheryl acetate, tetinyl palmitate, dimethicone, menthol, camphor, stearic acid, laureth-7, xanthan gum, polyacrylamide, C13-14 isoparaffin, corn oil, fragrance, DMDM hydantoin, iodopropynyl butylcarmamate, disodium EDTA, PG, and Ext. violet 2); the cation test formulation included strontium nitrate (500 mM) in the same Vaseline lactic acid lotion. 0.5 g of test and control solutions were applied with gloved fingers to the right and left calves. Subjects were asked to rate levels of irritation (sting, burn or itch) on the right calves, and irritation scores were recorded every minute for 10 minutes.

Figure 21:
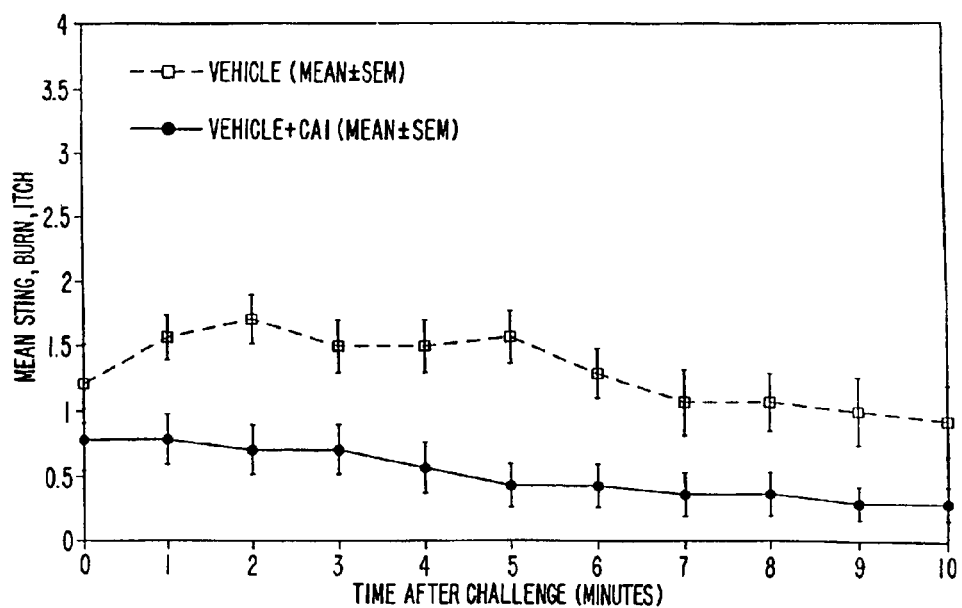
FIGS. 21 through 24 depict experimental data showing the time course of irritation responses (FIG. 21), the cumulative irritation over time (FIG. 22), and the subject-by-subject cumulative irritation suppression and irritation responses (FIGS. 23 and 24) for a panel of humans treated with 500 mM strontium nitrate (and control) in a post-shaving lactic acid skin irritation challenge.
Figure 22:
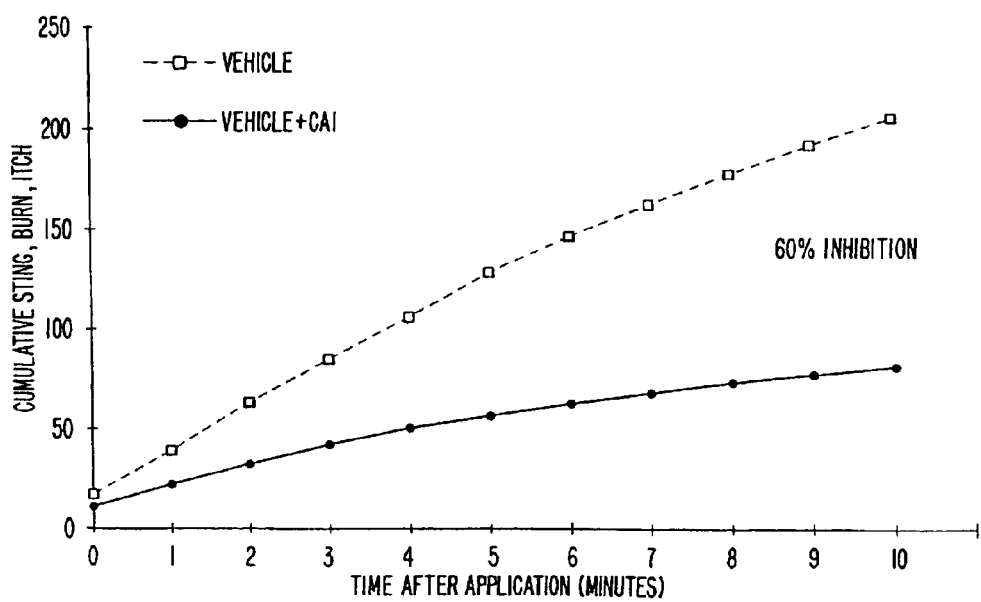
Figure 23:
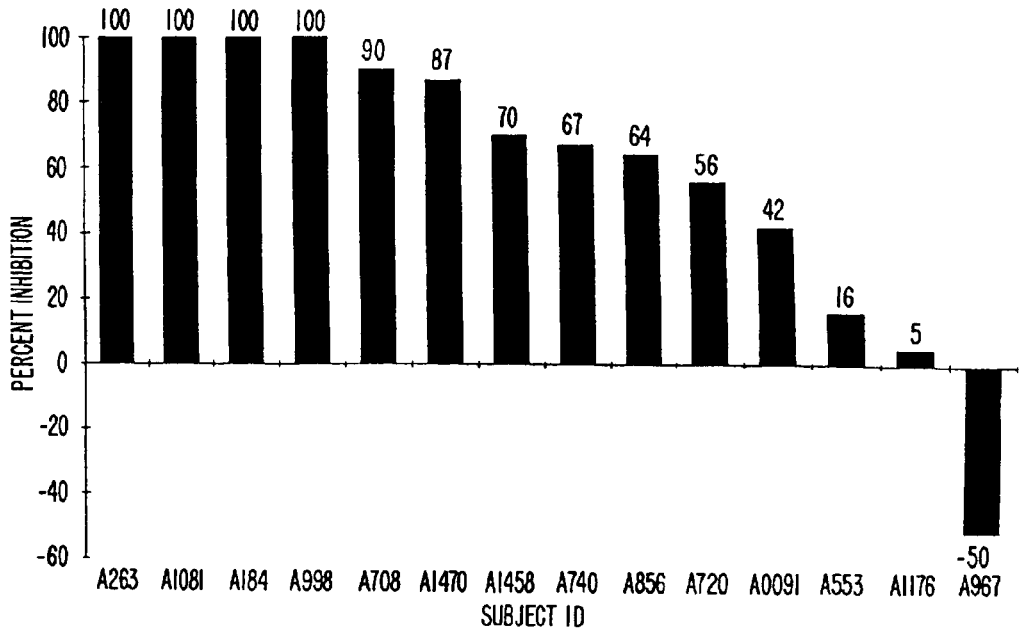
Figure 24:
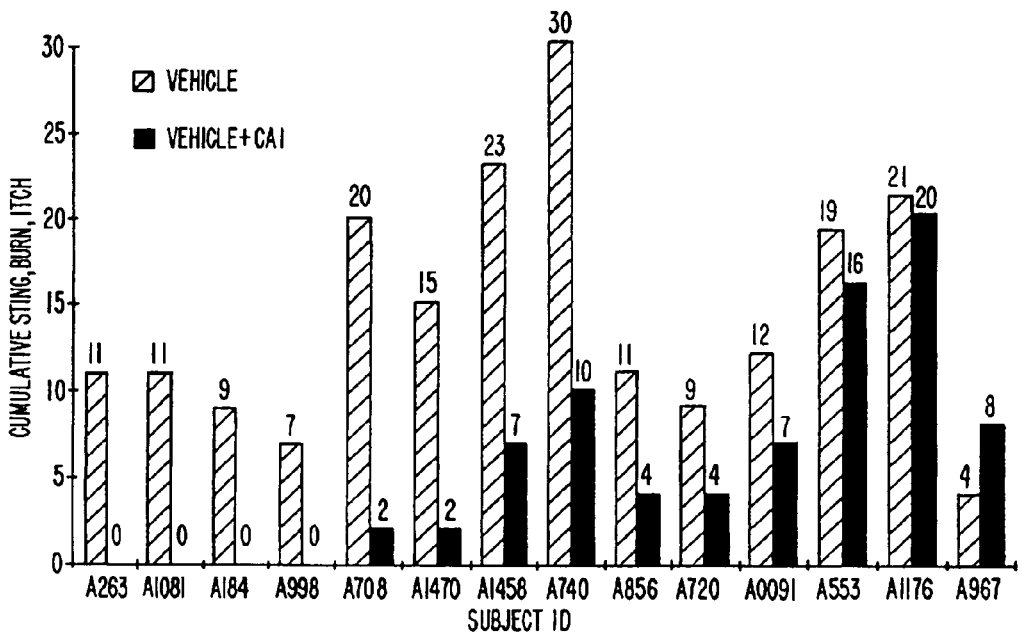

Irritation scores were cumulated for each individual and for the panel as a whole. FIG. 21 shows the time course of differential irritation responses for both cation-treated and non-treated (control) skin portions for the panel. FIG. 22 shows the cumulative irritation over time for the same panel, while FIGS. 23 and 24 show cumulative irritation suppression and treated/untreated irritation responses on a subject-by-subject basis.

Example 2

Dose-Response Studies

Figure 25:
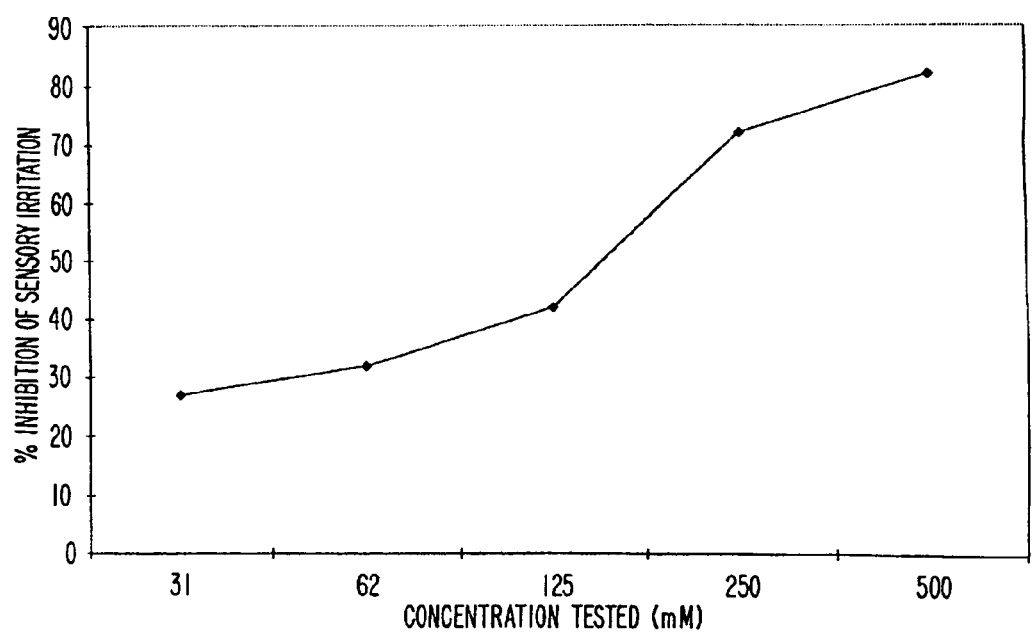
FIG. 25 depicts experimental data showing the cumulative irritation inhibition effects of strontium nitrate administered at varying concentrations (31-500 mM) in a lactic acid skin irritation challenge.

Additional studies of anti-irritant activity using varying concentrations of strontium cations were conducted in order to assess the dose-response behavior of the present formulations. The lactic acid irritation protocol described above was used, in which the anti-irritant cation component was strontium nitrate (31-500 mM). Cumulative irritation inhibition data are set forth in the following table, and are depicted graphically in FIG. 25.

| Concentration (mM) | Percent Inhibition |
|---|---|
| 31 | 27 |
| 62 | 32 |
| 125 | 42 |
| 250 | 72 |
| 500 | 82 |

Example 3

Additional Formulation Examples

Cation salts of the invention were formulated at various concentrations in a number of commercially available topical vehicles, and also in various commercially available topical cosmetic products. The resulting mixtures generally did not alter the texture, color, consistency or other physical properties of the product, and could be used as formulations to inhibit topical irritation.

a. Silicone-Based Vehicles

A 500 mM strontium nitrate topical lotion was prepared as follows. 10.58 g of strontium nitrate was dissolved in 55 ml of deionized water. This solution was combined with 10 ml cyclomethicone (Dow Corning, "DC344"), 20 ml cyclomethicone/dimethiconol (Dow Corning, "DC1401") and 15 ml cyclomethicone/dimethicone copolyol (Dow Corning, "DC3225C") and blended for 2-3 minutes. Imidizolidinyl urea (0.5%) was added as a preservative. An opaque white lotion (100 ml) resulted which, when applied to the skin of a fair (olive) skinned individual left no visible residue.

A 500 mM strontium nitrate topical gel was prepared as follows. 5.29 g of strontium nitrate was dissolved in 17 ml of deionized water. This solution was combined with 10 ml cyclomethicone (Dow Corning, "DC344"), 7.5 ml cyclomethicone/dimethiconol (Dow Corning, "DC1401"), 7.5 ml cyclomethicone/dimethicone copolyol (Dow Corning, "DC3225C") and 8 ml PEG-8 and blended for 2-3 minutes. Imidizolidinyl urea (0.5%) was added as a preservative. A clear, thick gel resulted (50 ml).

A 1500 mM strontium nitrate topical gel was prepared as follows. 31.75 g of strontium nitrate was dissolved in 50 ml of deionized water. This solution was combined with 10 ml cyclomethicone (Dow Corning, "DC344"), 20 ml cyclomethicone/dimethiconol (Dow Corning, "DC1401") and 20 ml cyclomethicone/dimethicone copolyol Maw Corning, "DC3225C") and blended for 2-3 minutes. Imidizolidinyl urea (0.5%) and benzyl alcohol (1%) were added as preservatives. A clear, thick gel resulted (100 ml) which, upon application to the skin of a fair-Skinned subject, left a visible white residue.

A 1500 mM strontium nitrate topical gel with a glycerin component was prepared as follows. 31.75 g of strontium nitrate was dissolved in 60 ml of deionized water. This solution was combined with 5 ml cyclomethicone (Dow Corning, "DC344"), 10 ml cyclomethicone/dimethiconol (Dow Corning, "DC1401"), 15 ml cyclomethicone/dimethicone copolyol (Dow Corning, "DC3225C") and 10 ml glycerin and blended for 2-3 minutes. Imidizolidinyl urea (0.5%) was added as a preservative. A clear, thick gel resulted (100 ml).

b. Commercial Cosmetic Vehicles

Topical solution forms of strontium nitrate, strontium chloride and strontium acetate were prepared by combining various amounts of the named salts with Elizabeth Arden Visible Difference Refining Toner (an alcohol-containing solution). The concentrations achieved were shown to be effective to inhibit skin irritation as described in the protocols set forth above.

Similarly, other solution forms of strontium nitrate were prepared by combining anti-irritant effective amounts of the salt with Estee Lauder Clean Finish Purifying Toner Normal/Dry, Oil of Olay Refreshing Toner Cleanser and Toner, Mary Kay Refining Refreshener Formula 2, Clearasil Clearstick Max Strength, and Oxy-10 Benzoyl Peroxide Wash.

Topical lotion forms of strontium nitrate were prepared by combining anti-irritant effective amounts of the salt with Cheseborough-Ponds Lotions (CCB-3-83-L15), Vaseline Intensive Care Lotion Smooth Legs and Feet, and Lubriderm Moisture Recovery Lotion. Similarly, serum and cream forms of strontium nitrate were prepared by combining anti-irritant effective amounts of the salt with Mary Kay Revival Serum (with 15% lactic acid) and L'Oreal Vichy Novactia Cream (with 2% capryloyl salicylic acid), respectively.

Other examples of topical product formulations comprising the anti-irritant strontium cation in various product forms and categories are provided in the Examples below. In the examples that follow, formulation ingredients are listed according to their chemical or proprietary name (left column) as well as their designation according to the Cosmetic, Toiletry and Fragrance Association (CTFA). In addition, one example of a specific percentage (% w/w) of each of the ingredients is shown (second column from right), as well as the most highly preferred range of concentrations of each ingredient (rightmost column). The percentages of the ingredients can be varied within the most highly preferred ranges specified in the right column without any significant effect on the aesthetic or performance characteristics of these formulations. Although the examples specify only selected formulations useful according to this invention, it should be understood that the following examples are illustrative only, and the present invention is not limited to the examples disclosed herein. The various ingredients (and their formulation percentages) may be varied within or beyond the ranges suggested herein according to general guidelines known in the art given the teachings of the present disclosure.

In addition, the following Examples provide processing steps and techniques that are especially useful in overcoming formulation difficulties associated with high salt concentration products, particularly emulsion system forms, such as gels, lotions and creams.

Example 4

Gel/Serum

Lactic Acid AHA Formulation; Final pH=3.2

| INGREDIENT | CTFA DESIGNATION | EXEMPLARY % WT/WT | PREFERRED RANGE % WT/WT |
|---|---|---|---|
| Deionized Water | Water | 61.55 | 60-65% |
| 1,3-Butylene Glycol | Butylene Glycol | 5.00 | 3-5% |
| Tween 20 | Polysorbate 20 | 1.00 | 0.5-1.5% |
| Germaben II | Propylene Glycol, Diazolidinyl Urea, Methylparaben, Propylparaben | 1.00 | 0.5-1.0% |
| Cellosize HEC QP52,000-H (Amerchol) | Hydroxyethyl cellulose | 0.60 | 0.4-0.8% |
| Lactic Acid, 85% | Lactic Acid | 17.25 | 1-20% |
| Strontium Nitrate | Strontium Nitrate | 5.00 | 0.5-6% |
| Sodium Hydroxide (20% soln) | Sodium Hydroxide | 8.60 | 0.5-10% |

The butylene glycol, Germaben II and Cellulose HEC were mixed to form a slurry and were then added to the already agitating water. The resulting mixture was heated to 60-65° C. and mixed until a clear viscous gel-like solution formed. Tween 20 was then added and dispersed in the solution while reducing the batch temperature to 40-45° C. The lactic acid and sodium hydroxide solutions were mixed together and added to the resulting solution and mixed until the ingredients were completely dispersed. The strontium nitrate was then added and mixed until completely dissolved, and the batch temperature was reduced to 25-30° C.

The final pH of this formulation was adjusted to approximately 3.2 with sodium hydroxide in order to maximize the exfoliating activity of the lactic acid while maintaining the anti-irritant properties of the strontium cation. Moisturizing properties in this formulation are derived from the combination of butylene glycol and the small amounts of lactate salt which formed at pH 3.2; this combination optimizes moisturization while not being sticky or tacky on the skin, when combined with the nonionic polymer gum Cellosize. While Germaben II was used as a preservative in this Example, other preservatives, including sorbic acid, benzyl alcohol, sodium benzoate, or dichlorobenzyl alcohol (or combinations thereof), would be useful.

This gel/serum formulation is also useful as the basis for the formulation of other gel products such as aftershaves or skin-conditioning gels by adjusting the level of the lactic acid, optionally together with the addition of fragrance or other moisturizers or skin-conditioning ingredients. The pH of the system is also adjustable to other levels more appropriate for toiletry and skin care products.

In clinical trials conducted on 24 subjects using two gel/serum formulations (12 subjects for each of two gel/serum formulations containing 15% lactic acid with a pH=3.2, similar to the gel/serum formulation of this Example), we observed 59% and 86% inhibition for the two formulations compared to Ponds Age Defying Complex™ (8% glycolic acid, pH=3.8).

Example 5

Toner/Skin Conditioner

Final pH=4.0

| INGREDIENT | CTFA DESIGNATION | EXEMPLARY % WT/WT | PREFERRED RANGE % WT/WT |
|---|---|---|---|
| Deionized Water | Water | 83.75 | 80-85% |
| Ethanol, anyhydrous | Ethyl alcohol | 7.0 | 5-10% |
| Glycerin | Glycerin | 0.50 | 0.1-3% |
| Polysorbate 20 | Polysorbate 20 | 0.50 | 0.1-1% |
| Lactic Acid (85%) | Lactic Acid | 0.50 | 0-5% |
| Strontium Nitrate | Strontium Nitrate | 5.00 | 0.5-6% |
| Phospholipid PTC | Cocamidopropyl Phosphatidyl PG - Dimonium Chloride | 1.00 | 0.5-2% |
| Benzyl alcohol | Benzyl alcohol | 1.00 | 0.5-1.5% |
| Sodium Hydroxide (20% soln) | Sodium Hydroxide | 0.75 | 0.5-1% |

All the ingredients, except for strontium nitrate, were mixed to form a clear solution. Strontium nitrate was then added and mixed until completely dissolved.

Optionally, the resulting formulation mixture is filtered to remove undissolved materials. In the above toner formulation, the combination of Phospholipid PTC and Polysorbate 20 enabled a clear solution to form. Without this combination of surfactants, the addition of 5.0% strontium nitrate would produce a cloudy suspension at pH=4.0. The cationic phospholipid also provides conditioning to the skin as well as effective antimicrobial activity. The level of alcohol was adjusted to a level that provided mild astringency without causing burning or stinging. Moisturization in this formulation is provided by the phospholipid, glycerin and sodium lactate (formed by the reaction of lactic acid with sodium hydroxide). The benzyl alcohol provides preservation as well as a mild floral masking scent.

The toner formulation provided in this Example also provides a basis to develop aftershave bracers/tonics or lotions, by for example increasing the level of alcohol in the formulation to 20-25%, while reducing the level of water in a similar amount, and adding a small amount of fragrance. The surfactants together with the alcohol would solubilize the fragrance. Similarly, a cologne or perfume may be formulated by simply adjusting the level of alcohol, water, and surfactants in the formulation, and adding the desired fragrance.

Example 6

Facial Cleanser

Final pH=5.4

| INGREDIENT | CTFA DESIGNATION | EXEMPLARY % WT/WT | PREFERRED RANGE % WT/WT |
|---|---|---|---|
| Standapol EA-2 | Ammonium laureth sulfate | 30.00 | 28-32% |
| Versene Na2 | Disodium EDTA | 0.05 | 0.01-0.1% |
| Velvetex BK-35 | Cocamidopropyl betaine | 8.00 | 6-9% |
| Phospholipid PTC | Cocamidopropyl Phosphatidyl PG - Dimonium Chloride | 2.00 | 1-3% |
| Cocamide DEA | Cocamide DEA | 2.00 | 1-3% |
| Lactic Acid (85%) | Lactic Acid | 0.10 | 0-3% |
| Glycerin | Glycerin | 3.00 | 1-5% |
| Germaben II | Propylene glycol, imidazolidinyl urea, methylparaben, propylparaben | 1.00 | 0.5-1.0 |
| Deionized Water | Water | 53.695 | 50-55% |
| Strontium Nitrate | Strontium Nitrate | 0.010 | 0.001-0.02% |
| Citric Acid | Citric Acid | 0.145 | 0.1-0.2% |

Water, Versene, lactic acid, glycerin, Germaben and strontium nitrate were added in that order to a container and mixed moderately to form mixture A. In a separate container, the Standapol, Velvetex, Phospholipid PTC and cocamide DEA were slowly mixed until completely blended to form a clear viscous blend B. While slowly mixing A, blend B was gradually added to A, and mixing was continued until a clear viscous solution resulted. Citric acid was added to adjust the pH to 5.4.

In this formulation, the cocamidopropyl betaine enables the Standapol EA-2, an anionic surfactant, which is normally incompatible with strontium nitrate, to be mixed together and allows the cleanser formulation to remain clear. The addition of Phospholipid PTC provides additional clarity to the system while also acting as a skin conditioning agent. The phospholipid also enhances the antimicrobial activity provided by the preservative Germaben. The combination of surfactants (Standapol EA and cocamidopropyl betaine), together with the Phospholipid PTC and cocamide DEA, yielded a mild, high-foaming product that effectively cleans and conditions the skin. Skin moisturization is derived from a combination of lactate, glycerin and phospholipid PTC.

Similar and/or related-type products may be formulated based on this Example, to provide cleansing and conditioning of the hair and body, as in commonly used shampoos, hand and body soap and bath cleansing products (e.g., bubble bath products). Various combinations of the surfactants (with or without additional surfactants) may be used to optimize cleansing conditions for each particular product. In addition, supplemental conditioners such as proteins or protein derivatives, or lanolin derivatives or vitamins, herbal extracts or cationic conditioners, may be added to provide unique formulations.

Example 7

Cream

Lactic Acid AHA Formulation; Final pH=3.2

| INGREDIENT | CTFA DESIGNATION | EXEMPLARY % WT/WT | PREFERRED % WT/WT |
|---|---|---|---|
| Incroquat Behenyl TMS | Behentrimonium Methosulfate, Cetearyl Alcohol | 2.00 | 0.5-4.0% |
| Miglyol 840 (Huls) | Propylene Glycol Dicaprylate/Dicaprate | 10.00 | 5-10% |
| Arlacel 165 | Glyceryl stearate & PEG-100 stearate | 8.00 | 5-12% |
| Dow Corning 556 | Phenyl Trimethicone | 2.00 | 0.5-4% |
| Glycerin | Glycerin | 3.80 | 0.5-6% |
| Germaben II (ICI) | Propylene Glycol, Diazolidinyl Urea, Methylparaben, Propylparaben | 1.00 | 0.5-2% |
| Xanthan Gum | Xanthan Gum | 0.20 | 0.05-2% |
| Veegum Ultra | Magnesium aluminum silicate | 0.40 | 0.05-5% |
| Spheron L1500 | Silica | 0.50 | 0.05-3% |
| Tween 60 | Polysorbate 60 | 1.00 | 0.05-2% |
| Lactic Acid, 85% | Lactic Acid | 17.25 | 1-20% |
| Sodium Hydroxide (20% soln.) | Sodium Hydroxide | 11.70 | 0.5-12% |
| Strontium Nitrate | Strontium Nitrate | 5.00 | 0.5-6% |
| Dow Corning 1401 fluid | Cyclomethicone, Dimethiconol | 1.00 | 0.5-2% |
| Deionized Water | Water | 36.15 | 30-70% |

The Veegum, xanthan gum, glycerin and Germaben were mixed together to form a slurry, and this mixture was added to the water (heated to 70-75° C.) and mixed until completely hydrated. To this was added the previously mixed lactic acid and sodium hydroxide solutions. Strontium nitrate was then added, and mixing continued until the strontium nitrate was completely dissolved (Mixture A). The Miglyol, Spheron, Arlacel, Incroquat Behenyl TMS, Tween 60, Dow Corning 556 were separately mixed together and heated to 70-75° C., melting all solids, and this mixture was added to A. While continuing to mix, the batch temperature was reduced to 55-60° C. The Dow Corning 1401 was added and mixed until fully dispersed. The entire batch was then homogenized for 5 minutes and the batch temperature was reduced to 25-30° C.

This Example demonstrates the use of strontium nitrate in an emulsion formulation. We have determined that nonionic and cationic emulsifiers, and especially combinations thereof, are compatible with strontium nitrate in emulsion systems. By varying the ratio of the emulsifiers, the viscosity of the emulsion can be controlled and regulated. Additional emulsion stability and variance of viscosity may be achieved by using nonionic gums such as xanthan gum, together with Veegum and silica. Sodium hydroxide was used to adjust the pH to 3.2 to optimize the efficacy of the lactic acid as an exfoliant while providing optimal functionality of strontium nitrate as an anti-irritant. While Germaben was used as the preservative in this Example, other preservatives which would function equally well at this pH include sorbic acid, dichlorobenzyl alcohol, benzoic acid, or a combination thereof. Similarly, while glycerin was used in this Example as a moisturizer, other humectants such as propylene glycol, butylene glycol or carbowaxes could have been used in this formulation.

In clinical trials conducted on 12 subjects using a cream formulation containing 15% lactic acid with a pH=3.2, similar to the cream formulation of this Example, we observed 61% inhibition compared to Ponds Age Defying Complex™ (8% glycolic acid, pH=3.8).

Example 8

Lotion

Lactic Acid AHA Formulation; Final pH=3.2

| INGREDIENT | CTFA DESIGNATION | EXEMPLARY % WT/WT | PREFERRED RANGE % WT/WT |
|---|---|---|---|
| Veegum Ultra | Magnesium Aluminum Silicate | 0.40 | 0.2-0.5 |
| Xanthan Gum | Xanthan Gum | 0.20 | 0.1-0.3 |
| Arlacel 165 | Glyceryl stearate & PEG-100 stearate | 8.00 | 5-10 |
| Tween 60 | Polysorbate 60 | 1.00 | 0.5-2.0 |
| Lanette O (Henkel) | Ceteareth Alcohol | 1.00 | 0.5-2.0 |
| Germaben II (ICI) | Propylene Glycol, Diazolidinyl Urea, Methylparaben, Propylparaben | 1.00 | 0.5-2.0 |
| Glycerin | Glycerin | 5.00 | 2-6 |
| Miglyol 840 (Huls) | Propylene Glycol Dicaprylate/Dicaprate | 10.00 | 8-12 |
| Dow Corning 556 | Phenyl Trimethicone | 2.00 | 1-3 |
| Dow Corning 1401 fluid | Cyclomethicone & Dimethiconol | 1.00 | 0.5-2.0 |
| Lactic Acid (85%) | Lactic Acid | 17.25 | 1-20 |
| Sodium Hydroxide (20% soln.) | Sodium Hydroxide | 11.70 | 0.5-13 |
| Strontium Nitrate | Strontium Nitrate | 5.00 | 0.5-6 |
| Deionized Water | Water | 36.45 | 35-38 |

The Veegum, xanthan gum, glycerin and Germaben were mixed into a slurry, and this slurry was added gradually to the agitating water (heated to 70-75° C.) and mixed until all the gums were thoroughly dispersed (Mixture A). In a separate container, the Miglyol, Spheron, Arlacel, Lanette 0, Tween and Dow Corning 0.556 were heated to 70-75° C. and mixed, melting all solids in the mixture to form Mixture B. With moderate mixing, Mixture B was added to A and mixed until a uniform emulsion was formed, and the temperature of the resulting emulsion was reduced to 55-60° C. The Dow Corning 1401 fluid was then added and mixed until completely dispersed. To this was added a mixture of the lactic acid and the sodium hydroxide solution, while mixing until completely dissolved. The batch temperature was then reduced to 25-30° C.

In clinical trials conducted on 24 subjects using two lotion formulations (12 subjects for each of two lotion formulations containing 15% lactic acid with a pH=3.2, similar to the lotion formulation of this Example), we observed 26% and 37% inhibition for the two formulations compared to Ponds Age Defying Complex™ (8% glycolic acid, pH=3.8).

Example 9

Liquid Makeup Foundation

| INGREDIENTS | EXEMPLARY % WT/WT | PREFERRED RANGE % WT/WT |
|---|---|---|
| Part A | | |
| Isostearyl Neopentanoate | 5.00 | 4-6.0 |
| Isocetyl Stearate | 9.00 | 5-10.0 |
| Triisocetyl Citrate | 5.00 | 3-6.0 |
| Generol 122E | 2.00 | 1-3.0 |
| Glyceryl Stearate | 1.60 | 1-3.0 |
| Generol 122 | 1.50 | 0.5-3.0 |
| Dimethicone (100 Vis) | 1.00 | 0.5-3.0 |
| Propylparben | 0.15 | 0.5-0.15 |
| Part B | | |
| Strontium Nitrate | 2.00 | 1-3.0 |
| Cocamido Propyl Betaine | 1.00 | 0.5-2.0 |
| Disodium Oleamido PEG Sulfosuccinate | 0.90 | 0.5-1.0 |
| Magnesium Aluminum Silicate | 0.40 | 0.1-0.5 |
| Xanthan Gum | 0.20 | 0.1-0.5 |
| Propylene Glycol | 6.00 | 3-6.0 |
| Glycerin | 2.00 | 1-3.0 |
| Disodium EDTA | 0.10 | 0.05-0.10 |
| Imidazolidinyl Urea | 0.30 | 0.2-0.30 |
| Methylparaben | 0.25 | 0.1-0.30 |
| Sodium Dehydroacetate | 0.20 | 0.05-0.2 |
| Lactic Acid | 3.00 | 0-5.0 |
| Purified Water | 47.28 | 45-60.0 |
| Part C | | |
| Iron Oxides | 2.50 | 1-3.0 |
| Titanium Dioxide | 7.50 | 5-10.0 |
| Part D | | |
| Sodium Hydroxide (20% sol.) or Citric Acid | q.s. to pH 5.0-5.5 | |

Part A is heated to 70-75° C. In a separate container, the magnesium aluminum silicate, xanthan gum, propylene glycol, and glycerin of Part B are mixed together and dispersed completely in the water. The strontium nitrate of Part B is then added and mixing is continued until completely dissolved. The remaining ingredients of Part B are added and the batch is heated to 70-75° C. The pigments of Part C are micronized and added to Part A with mixing until uniform. The Part A/C mixture is added to Part B with agitation. The final pH is adjusted to 5.0-5.5 using sodium hydroxide and/or citric acid. Mixing is continued and the batch is cooled to 25-30° C.

The nonionic emulsifiers (Generol 122, Generol 122E and glyceryl stearate) are compatible with and provide a stable emulsion system. The Generol emulsifiers also act as dispersants for the pigments in the system; glyceryl stearate also acts as a viscosity builder for the emulsion. These emulsifiers are designed to tolerate high concentrations of alpha hydroxy acids in a given formulation and remain stable. The use of a betaine provides compatibility of an anionic surfactant (sulfosuccinate) with the formulations of the present invention. The sulfosuccinate surfactant also functions as an effective setting agent and dispersant for the pigments. Emollience in this makeup formulation is provided by the combination of isostearyl neopentanoate, isocetyl stearate, and triisocetyl citrate, which is stable at relatively low pH and compatible with strontium nitrate. Additional emollience is derived from the use of a silicone (dimethicone) which is also stable at acidic pH and compatible with strontium nitrate. Veegum and xanthan gum are used to build viscosity in the emulsion, help suspend the pigments and stabilize the emulsion system. Glycerin and propylene glycol function as stable moisturizers, and propylparaben, together with methylparaben and sodium dehydroacetate, provides a preservative system for the formulation.

Other liquid color makeup or cosmetic products and a variety of pigmented emulsion-type products can be produced on the basis of this Example by varying the levels and types of pigments used in the formulation. Sunscreens containing titanium dioxide and/or zinc oxide may also be developed utilizing same formulation, except for the substitution of these oxides for the pigments specified in Part C of the Example. Other skin conditioners such as lanolin or lanolin derivatives, or vitamins or herbal derivatives may also be added to the formulation. Pre-sun or sunless tanning products such as those containing dihyroxyacetone can also be developed utilizing similar formulation guidelines. Combination sunscreen products containing pigments or physical blocking agents, together with chemical sunscreens (UV absorbers) or a combination thereof, may easily be developed from this general recipe with appropriate modifications.

Example 10

Hair Conditioner/Scalp Protectant

| INGREDIENTS | CTFA DESIGNATION | EXEMPLARY % WT/WT | PREFERRED RANGE % WT/WT |
|---|---|---|---|
| Part A | | | |
| Deionized Water | Water | 91.20 | 89-92 |
| Strontium Nitrate | Strontium Nitrate | 1.00 | 0.5-6.0 |
| Busan 1504 | Dimethyl Hydroxymethyl Pyrazole | 0.10 | 0.05-0.5 |
| Panthenol | Panthenol | 0.25 | 0.1-0.3 |
| Disodium EDTA | Disodium EDTA | 0.05 | 0.02-0.1 |
| Promulgen D | Cetearyl Alcohol (and) Ceteareth-20 | 1.10 | 1-2 |
| Stearyl Alcohol | Stearyl Alcohol | 5.00 | 4-6 |
| Cetrimonium Bromide | Cetrimonium Bromide | 5.00 | 4-6 |
| Jojoba Oil | Jojoba Oil | 0.30 | 0.2-0.5 |
| Part B | | | |
| Acetamide MEA | Acetamide MEA | 1.00 | 0.5-2.0 |
| Lactamide MEA | Lactamide MEA | 1.00 | 0.5-2.0 |

The strontium nitrate and the Busan 1504 are dissolved and mixed in the water and then heated to 70-75° C. The remaining ingredients of Part A are then added (in the order indicated) with mixing until completely dispersed. The resulting mixture is cooled to 40° C. The ingredients of Part B are added with mixing until completely dispersed. Mixing is continued and the batch temperature is reduced to 25-30° C.

This formulation utilizes a combination of nonionic and cationic emulsifiers in order to make strontium nitrate compatible in this system and to provide stability to the formulation. The nonionic emulsifiers also provide thickening activity to the formulation. Further hair conditioning and hair sheen is derived from the jojoba oil in the formulation. Additional hair conditioning is provided by the acetamide MEA and lactamide MEA. Other conditioning agents such as proteins and protein derivatives, vitamins or even UV absorbers could be added to this formulation for additional benefits. Similar formulations can easily be made from this Example, including the addition of dyes to impart color to the hair. Small amounts of alpha hydroxy acids such as lactic, glycolic, citric or malic acids could also be added to the formulation as moisturizers or conditioners of the scalp to provide enhanced aesthetics and more desirable conditioning activity.

Example 11

Antiperspirant/Deodorant Solution

| INGREDIENT | CTFA DESIGNATION | EXEMPLARY % WT/WT | PREFERRED RANGE % WT/WT |
|---|---|---|---|
| Reach 501 Solution | Aluminum Chlorohydrate | 36.10 | 10-40 |
| Alcohol SDA 40 | SD Alcohol 40 | 28.00 | 25-35 |
| Transcutol | Ethoxydiglycol | 10.00 | 5-10 |
| Tween 20 | Polysorbate 20 | 1.00 | 0.5-1.00 |
| Phospholipid PTC | Cocamidopropyl-Phosphatidyl PG-Dimonium Chloride | 1.00 | 1-2 |
| Deionized Water | Water | 20.90 | 20-25 |
| Strontium Nitrate | Strontium Nitrate | 5.00 | 0.5-10 |

The water, Polysorbate 20, Phospholipid PTC and Transcutol are mixed together. The strontium nitrate is added and mixed until completely dissolved. The resulting mixture is added to the previously mixed aluminum chlorohydrate and SD alcohol 40, and mixing is continued to form a solution.

The combination of ethoxydiglycol, Polysorbate 20 and Phospholipid PTC is utilized to maintain the strontium nitrate in solution. By doing so, the irritation potential of the aluminum chlorohydrate and/or the alcohol to the skin is reduced. Variations of this Example may be formulated in different physical forms by adding various waxes to the liquid antiperspirant to develop a stick-like product, or various gel-producing ingredients can be used to form a gel. Cream and lotion form antiperspirants can be made using standard emulsion forming techniques. In addition, aluminum chlorohydrate may be replaced with a deodorant active such as triclosan by adjusting the ratio of alcohol to water to compensate for the lower level of deodorant active used in the system. In this manner, a full range of deodorant products such as sticks, gels, lotions or creams can be formulated based on this Example.

Example 12

Creamy Lipstick Formulation

| INGREDIENTS | EXEMPLARY % WT/WT | PREFERRED RANGE % WT/WT |
|---|---|---|
| Part A | | |
| Castor Oil | 38.00 | 30-40 |
| Isopropyl Lanolate | 10.00 | 5-15 |
| Mica | 5.80 | 4-6 |
| Titanium Dioxide | 3.50 | 3-6 |
| Iron Oxides | 2.50 | 0.5-4 |
| FD&C Colors | 6.00 | 3-7 |

-continued

| INGREDIENTS | EXEMPLARY % WT/WT | PREFERRED RANGE % WT/WT |
|---|---|---|
| Part B | | |
| Isopropyl Lanolate | 12.00 | 8-15 |
| Candelilla Wax | 9.00 | 7-10 |
| Isostearyl Neopentanoate | 6.50 | 3-10 |
| Beeswax | 1.50 | 0.5-5 |
| Microcrystalline Wax | 1.00 | 0.5-5 |
| Carnauba Wax | 0.80 | 0.4-1 |
| Propylparaben | 0.20 | 0.05-0.3 |
| BHT | 0.10 | 0.01-0.1 |
| Tocopherol | 0.10 | 0.05-0.5 |
| Part C | | |
| Strontium Nitrate | 3.00 | 0.5-6 |

The ingredients of Part A are mixed together and passed through a three-roller mill until all pigments are completely extended, and the mixture is then heated to 85° C. In a separate container, the ingredients of Part B are mixed together and heated to 85° C. Part A is added to Part B and mixed until homogeneous. Mixing is continued and the batch is cooled to 72° C. The strontium nitrate is then added and mixing is continued until completely dispersed. The final mixture is poured into molds and cooled to room temperature.

Example 13

Hair Straightener/Relaxer

Final pH=11-13.5

| INGREDIENTS | CTFA DESIGNATION | EXEMPLARY % WT/WT | PREFERRED RANGE % WT/WT |
|---|---|---|---|
| Part A | | | |
| Polawax | Emulsifying Wax | 7.5 | 6-8 |
| Crodacol S-70 | Stearyl Alcohol | 2.5 | 1-3 |
| Crodacol C-70 | Cetyl Alcohol | 1.0 | 0.5-2 |
| Petrolatum | Petrolatum | 21.0 | 19-22 |
| Mineral Oil | Mineral Oil | 15.0 | 12-16 |
| Volpo S-2 | Steareth-2 | 0.5 | 0.5-1.0 |
| Volpo S-10 | Steareth-10 | 2.5 | 1-3 |
| Crodafos N-10 Neutral | DEA Oleth-10 Phosphate | 1.0 | 0.5-2.0 |
| Part B | | | |
| Deionized Water | Water | 42.0 | 40-45 |
| Propylene Glycol | Propylene Glycol | 3.0 | 2-5 |
| Strontium Nitrate | Strontium Nitrate | 4.0 | 0.5-6 |
| Part C | | | |
| Sodium Hydroxide | Sodium Hydroxide | 2.0 | 2-3 |

The ingredients of Part A are combined with mixing and heated to 70-75° C. The ingredients of Part B are combined in a separate container and heated to 70-75° C. Mixture B is added to A with moderate mixing and cooled to 40° C. The sodium hydroxide of Part C is slowly added to the resulting A/B mixture, the batch is cooled to 25-30° C., and homogenized. The pH of the formulation is then adjusted to pH=11-13.5 using the sodium hydroxide.

The strontium nitrate, together with the mineral oil and petrolatum, help alleviate the burning, itching, and stinging of the scalp due to the high level of alkali in this formulation. This level of alkali is necessary for the functional activity of the hair straightener/relaxer. Similar formulations may be prepared and used as permanents, where the hair is chemically "straightened" in the rolled position physically and then "restored" to its normal state of crosslinking while still in rollers to "permanently" leave it in the curled state.

Example 14

Anti-Irritant Lotion Without AHA

| INGREDIENTS | CTFA DESIGNATION | EXEMPLARY % WT/WT | PREFERRED RANGE % WT/WT |
|---|---|---|---|
| Part A | | | |
| Polawax | Emulsifying wax, N.F. | 10.0 | 5-15 |
| Incroquat Behenyl TMS | Behentrimonium Methosulfate, Cetearyl Alcohol | 3.0 | 1-5 |
| Ceraphyl 375 | Isostearyl Neopentanoate | 5.0 | 3-7 |
| Part B | | | |
| Germaben II (ICI) | Propylene Glycol, Diazolidinyl Urea, Methylparaben, Propylparaben | 1.0 | 0.1-2 |
| Strontium Nitrate | Strontium Nitrate | 5.0 | 0.5-6 |
| Glycerin | Glycerin | 3.0 | 1-6 |
| Deionized Water | Water | 73.0 | 65-80 |

The ingredients of Part A are mixed together and heated to 70-75° C., melting all solids. The ingredients of Part B are separately mixed together and heated to 70-75° C. With mixing, Mixture A is added to B and mixed until homogeneous. Mixing is continued and the batch is cooled to 25-30° C.

The combination of a nonionic emulsifier (polawax) with a cationic emulsifier (Incroquat Behenyl TMS) produces a stable emulsion in which the strontium nitrate is compatible for a neutral pH lotion. In addition, the cationic emulsifier produces an aesthetic skin feel which is quite pleasing. Strontium chloride can be substituted in place of strontium nitrate, or a combination of anti-irritants may be used. Other emollients could replace or be combined with the Ceraphyl 375 to modify the skin feel. For example, octyl stearate, hexadecyl alcohol, isocetyl stearate or mineral oil could replace the Ceraphyl 375 or be used in combination with it. Additionally, other moisturizers/humectants could be used in place of glycerin or in conjunction with it in the formulation, including propylene glycol, butylene glycol or various carbowaxes. Also, active ingredients could be added to the formulation, such as benzocaine or allantoin.

Example 15

Glycolic Acid Chemical Peel Solution or Gel

Final pH=0.5-2.7

| INGREDIENTS | CTFA DESIGNATION | EXEMPLARY % WT/WT | PREFERRED RANGE % WT/WT |
|---|---|---|---|
| Glycolic Acid (98%) | Glycolic Acid | 70.00 | 10-80 |

| INGREDIENTS | CTFA DESIGNATION | EXEMPLARY % WT/WT | PREFERRED RANGE % WT/WT |
|---|---|---|---|
| Purified Water | Purified Water | 22.40 | 20-70 |
| Hydroxyethyl-cellulose | Hydroxyethyl-cellulose | 0.6 | 0.4-1.0 |
| Strontium Nitrate | Strontium Nitrate | 10.0 | 4-15 |
| Butylene Glycol | Butylene Glycol | 2.0 | 1-5 |

The butylene glycol and hydroxyethylcellulose are mixed together to form a slurry, which is then added slowly to the water, and the temperature is adjusted to 60-65° C. while mixing until a clear viscous solution forms. The resulting mixture is cooled to 25-30° C. and the strontium nitrate is added, mixing until completely dissolved. The pH is adjusted to 0.5-2.7 using the sodium hydroxide.

Other alpha hydroxy acids could be substituted for glycolic acid, including lactic, malic, or citric acid. The formulation may also be modified to incorporate alcohol or preservatives.

Example 16

Gel without AHA

Final pH=5.5

| INGREDIENTS | CTFA DESIGNATION | EXEMPLARY % WT/WT | PREFERRED RANGE % WT/WT |
|---|---|---|---|
| Deionized Water | Water | 92.0 | 90-95 |
| Strontium Nitrate | Strontium Nitrate | 5.0 | 2-10 |
| Germaben II | Germaben II | 1.0 | 0.5-1.0 |
| Propylene Glycol | Propylene Glycol | 1.0 | 1-3 |
| Amigel | Sclerotium Gum | 1.0 | 0.5-2.0 |

The Germaben, propylene glycol and sclerotium gum are mixed together to form a slurry, which is slowly added to the water which has been heated to 60-65° C. and mixed until the gum is completely hydrated. The batch is cooled to 25-30° C. and the strontium nitrate is added and the batch is mixed until the strontium nitrate is completely dissolved.

Example 17

Non-Exfoliating ARA Moisturizing Cream

Final pH=4.5

| INGREDIENTS | CTFA DESIGNATION | EXEMPLARY % WT/WT | PREFERRED RANGE % WT/WT |
|---|---|---|---|
| Part A | | | |
| Deionized Water | Water | 34.55 | 30-40 |
| Trisodium EDTA | Trisodium EDTA | 0.10 | 0.05-0.1 |
| Natrasol 250HR | Hydroxyethylcellulose | 0.50 | 0.2-5 |
| Butylene Glycol | Butylene Glycol | 5.00 | 3-6 |
| Germaben II | Propylene Glycol, Diazolidinyl Urea, Methylparaben, Propylparaben | 1.00 | 0.5-1 |
| Veegum Ultra | Magnesium aluminum silicate | 0.70 | 0.3-0.8 |
| Part B | | | |
| Lactic Acid (88%) | Lactic Acid | 17.05 | 15-17 |
| Ammonium Hydroxide (28% sol'n) | Ammonium Hydroxide | 1.00 | 1-2 |
| Sodium Hydroxide (20% sol'n) | Sodium Hydroxide | 8.60 | 8-9 |
| Strontium Nitrate | Strontium Nitrate | 4.50 | 2-10 |
| Part C | | | |
| Cyclomethicone | Cyclomethicone | 7.0 | 5-7 |
| Dimethicone | Dimethicone | 3.0 | 2-5 |
| Spheron L1500 | Silica | 1.00 | 0.5-1 |
| Octyl Stearate | Octyl Stearate | 5.00 | 3-6 |
| Isocetyl Stearate | Isocetyl Stearate | 5.00 | 3-6 |
| PEG-40 Stearate | PEG-40 Stearate | 1.5 | 1-2 |
| Glyceryl Stearate | Glyceryl Stearate | 2.0 | 1-3 |
| Steareth-2 | Steareth-2 | 1.5 | 1-2 |
| Cetyl Alcohol | Cetyl Alcohol | 1.0 | 1-2 |

The Veegum, Natrasol, butylene glycol and Germaben are mixed together to form a slurry, which is then added to the already agitating water heated to 70-75° C. and mixed until completely dispersed and the gums are hydrated. To this is added a mixture of the ingredients of Pan B and mixing is continued until uniform mixture is obtained. The strontium nitrate is added and mixed until completely dissolved, maintaining the temperature at 70-75° C. to form Mixture A. In a separate container, the ingredients of Part C are mixed together and heated to 70-75° C., melting all solids, and then this mixture is added to Mixture A while continuing to mix and reducing the batch temperature to 50-55° C. The resulting mixture is homogenized and the batch temperature is reduced to 25-30° C. while mixing.

Example 18

Gel/Serum

Glycolic Acid AHA Formulation; Final pH=3.0

| INGREDIENTS | CTFA DESIGNATION | EXEMPLARY % WT/WT | PREFERRED RANGE % WT/WT |
|---|---|---|---|
| Deionized water | water | 57.30 | 50-60 |
| 1,3-Butylene glycol | Butylene glycol | 5.00 | 3-7 |
| Cellosize HEC qp-52,000 H | Hydroxyethyl cellulose | 0.60 | 0.1-1 |
| Glycolic acid | Glycolic acid, 98% | 15.30 | 1-20 |
| Strontium nitrate | Strontium nitrate | 5.00 | 2-6 |
| L-lysine | L-lysine | 5.00 | 1-6 |
| Germaben II | Propylene glycol, Imidazolidinyl urea Methylparaben, Propylparaben | 1.00 | 0.5-2 |
| Tween 20 | Polysorbate 20 | 1.00 | 0.5-2 |
| Fragrance | Belmay 1199460995 | 0.10 | 0.01-0.2 |
| Sodium hydroxide (20%) | Sodium hydroxide | qs to pH 3.0 | |

The butylene glycol and Germaben II were mixed together and heated to 45-50° C., mixing until completely dissolved. To this was added the hydroxyethylcellulose, and the batch was mixed gently and briefly until the cellulose wetted out. The resulting mixture was added to the already agitating water and mixing was continued until a clear gel (free of undispersed particles) was formed. After the gel was completely formed, it was cooled to 25-30° C. The glycolic acid was then added and the batch was mixed. The strontium nitrate was then added and mixed and the L-lysine was added and mixed until completely dissolved. The pH of the final mixture was adjusted to pH=3.0 using sodium hydroxide.

The L-lysine is added in this Example as an additional anti-irritant ingredient to be used in the formulation in combination with the strontium nitrate.

The foregoing examples are not intended to limit the scope of the present invention, which is set forth in the following claims. In particular, various equivalents and substitutions will be recognized by those skilled in the art in view of the foregoing disclosure, and these are contemplated to be within the scope of the invention.

What is claimed is:

1. A method for reducing irritation comprising the steps of:
   preparing a composition comprising:
      an aqueous-soluble strontium cation;
      a skin penetration enhancer; and
      a delivery vehicle; and
   topically administering the composition to keratinized skin.

2. The method according to claim 1, wherein the composition further comprises a counterion.

3. The method according to claim 2, wherein the counterion further comprises an inorganic anion.

4. The method according to claim 3, wherein the inorganic anion further comprises a halogen selected from the group consisting of: F, Cl, Br, and I.

5. The method according to claim 3, wherein the inorganic anion further comprises a nitrate.

6. The method according to claim 4, wherein the halogen is Cl.

7. The method according to claim 1, wherein the delivery vehicle is water.

8. The method according to claim 1, wherein the composition further comprises an organic solvent.

9. The method according to claim 8, wherein the organic solvent is a glycol.

10. The method according to claim 6, wherein the delivery vehicle is water.

11. The method according to claim 1, wherein the irritation results in stinging, burning, itching, redness, swelling or inflammation.

* * * * *